US008846078B2

(12) United States Patent
Commander et al.

(10) Patent No.: US 8,846,078 B2
(45) Date of Patent: Sep. 30, 2014

(54) BRUCELLOSIS DNA VACCINE

(75) Inventors: Nicola Commander, Surrey (GB); Stephen Spencer, Surrey (GB)

(73) Assignee: The Secretary of State for Environment, Food & Rural Affairs Acting through the Animal Health and Veterinary Laboratories Agency (GB)

( * ) Notice: Subject to any disclaimer, the term of this patent is extended or adjusted under 35 U.S.C. 154(b) by 1571 days.

(21) Appl. No.: 11/688,519

(22) Filed: Mar. 20, 2007

(65) Prior Publication Data

US 2007/0224257 A1 Sep. 27, 2007

Related U.S. Application Data

(60) Provisional application No. 60/783,833, filed on Mar. 21, 2006.

(51) Int. Cl.

| | |
|---|---|
| ***A61K 9/127*** | (2006.01) |
| ***A61K 39/02*** | (2006.01) |
| ***A61K 45/00*** | (2006.01) |
| ***G01N 33/569*** | (2006.01) |
| ***A61K 48/00*** | (2006.01) |
| *A61K 39/00* | (2006.01) |

(52) U.S. Cl.

CPC ...... *G01N 33/56911* (2013.01); *A61K 2039/53* (2013.01); *A61K 2039/55555* (2013.01); *G01N 2469/20* (2013.01); *A61K 39/098* (2013.01); *G01N 2333/23* (2013.01); *A61K 2039/57* (2013.01); *A61K 48/00* (2013.01); *A61K 9/127* (2013.01); *A61K 2039/6018* (2013.01)

USPC ...................... 424/450; 424/252.1; 424/283.1

(58) Field of Classification Search

None

See application file for complete search history.

(56) References Cited

FOREIGN PATENT DOCUMENTS

WO WO9324640 * 12/1993

OTHER PUBLICATIONS

Gregoriadis et al., Vaccine, 20, 5, B1-B9 2002.*

Al-Mariri et al., "Induction of Immune Response in BALB/c Mice with a DNA Vaccine Encoding Bacterioferritin or P39 of *Brucella* spp.", 2001, Infection and Immunity, pp. 6264-6270, vol. 69, No. 10.

Alton, "Control of *Brucella melitensis* infection in sheep and goats—a review", 1987, Tropical Animal Health and Production, pp. 65-74, vol. 19, No. 2.

Altschul et al., "Basic local alignment search tool", 1990, Journal of Molecular Biology, pp. 403-410, vol. 215, No. 5.

Brewer et al., "Lipid vesicle size determines the Th1 or Th2 response to entrapped antigen", 1998, Journal of Immunology, pp. 4000-4007, vol. 161, No. 8.

Cheville, "Development, testing and commercialization of a new Brucellosis vaccine for cattle", 2000, Annals of the New York Academy of Sciences, pp. 147-153, vol. 916.

Commander et al., Poster presentation at "DNA Vaccines 2002" Conference in Edinburgh, Scotland.

Commander et al., Poster presentation at NATO—Advance Research Workshop, "Bactarial Biological Warfare Agents" Conference in Bratislava, Slovakia, 2002.

Commander et al., Poster presentation at "Brucellosis 2003" Conference in Pamplona, Spain Sep. 15-17, 2003.

Commander et al., Poster presentation at "DNA Vaccine 2004" Conference in Monte Carlo, Monaco.

Garin-Bastuji et al., "*Brucella melitensis* infection in sheep: present and future", 1998, Veterinary Research, pp. 255-274, vol. 29, Nos. 3-4.

Leclerq et al., "Induction of a Th1-type of immune response but not protective immunity by intramuscular DNA immunisation with *Brucella abortus* GroEL heat-shock gene", 2002, Journal of Medical Microbiology, pp. 20-26, vol. 51.

Munoz-Montesino et al., "Intraspleen Delivery of a DNA Vaccine Coding for Superoxide Dismutase (SOD) of *Brucella abortus* Induces SOD-Specific CD4+ and CD8+ T Cells", 2004, Infection and Immunity, pp. 2081-2087, vol. 72, No. 4.

Murillo et al., "A *Brucella ovis* antigenic complex bearing poly-epsilon-carolactone microparticles confer protection against experimental brucellosis in mice", 2001, Vaccine, pp. 4099-4106, vol. 19, No. 30.

Needleman et al., "A general method applicable to the search for similarities in the amino acid sequence of two proteins", 1970, Journal of Molecular Biology, pp. 443-453, vol. 48, No. 3.

Velikovsky et al., "A DNA Vaccine Encoding Lumazine Synthase from *Brucella abortus* Induces Protective Immunity in BALB/c Mice", 2002, Infection and Immunity, pp. 2507-2511, vol. 70, No. 5.

Verger et al., "Taxonomy of the genus *Brucella*", 1987, Annals Institut Pasteur Microbiology, pp. 235-238, vol. 138, No. 2.

Westwood et al. "Epitope Mapping, a Practical Approach", 2000, pp. v-xv, Oxford University Press, Oxford, United Kingdom.

Pettersson, "Methods of epitope mapping", 1992, Molecular Biology Reports, pp. 149-153, vol. 16.

* cited by examiner

*Primary Examiner* — Nancy T Vogel

(57) ABSTRACT

Brucellosis is a disease caused by facultative intracellular bacteria of the monospecific genus *Brucella melitensis*. The invention in one aspect is an immunogenic nucleic acid composition comprising DNA encoding *Brucella melitensis* Invasion Protein B, a polypeptide with at least 95% identity thereto, or an immunologically active fragment of either of these, and an adjuvant. In another aspect, the invention is a DNA vaccine composition comprising a plasmid vector having DNA encoding a polypeptide as recited above, in which said plasmid vector is adsorbed to a liposome. Other aspects of the invention include methods of inducing an enhanced immune response to *Brucella* infection in an animal, methods for the differential diagnosis in an animal of brucellosis and vaccination by an immunogenic nucleic acid composition having DNA encoding any of the above-recited polypeptides, and a kit for conducting said differential diagnosis methods.

12 Claims, 3 Drawing Sheets

IalBspecific reactions

- L-pcDNA3.1
- L-p-ialB
- *p-ialB [X4]
- p-ialB
- pcDNA3.1 X 4
- pcDNA3.1
- PBS X 4
- PBS

Omp25 specific reactions

- Liposome only
- *L-omp25
- *p-omp25 X 4
- *p-omp25
- pcDNA3.1 X 4
- pcDNA3.1
- PBS X 4
- PBX 10,000   5000   0          100        200

*Antibody production*
reciprocal titre

*Brucella load*
% challenge dose

▨ IgG1   ▨ IgG2a   ■ Bacterial load

BRUCELLOSIS DNA VACCINE

CROSS-REFERENCE TO RELATED APPLICATION

This application claims priority to U.S. Provisional Application Ser. No. 60/783,833 filed on Mar. 21, 2006, which is hereby incorporated by reference in its entirety.

FIELD OF THE INVENTION

This invention relates to non-living vaccines for prophylactic and therapeutic treatment of brucellosis in an animal. The invention further relates to methods of inducing an enhanced immune response to *Brucella* infection in an animal, methods for the differential diagnosis in an animal of brucellosis and vaccination against brucellosis, and a kit for conducting said differential diagnosis methods.

BACKGROUND OF THE INVENTION

Brucellosis is a worldwide zoonosis of considerable social and economic importance. It is considered by the Food and Agriculture Organisation (FAO) and World Health Organisation (WHO) to be the most widespread zoonosis in the world, and is on the Office International des Epizooties (OIE) List B, denoting diseases of significant socio-economic, public health and international trade importance. The causative agents of the disease are facultative intracellular bacteria of the monospecific genus *Brucella melitensis*. Despite extensive genetic homogeneity amongst strains, historical classification defines six separate species, *B. melitensis, B. abortus, B. suis, B. ovis, B. canis* and *B. neotomae*, and a multitude of phenotypically defined sub-species or biovars (reviewed in Verger et al., 1987, Ann. Inst. Pasteur Microbiol. 138: 235-238). This nomenclature remains common practice amongst researchers in the field, and has epidemiological and clinical relevance. *Brucella* infections can be found in a wide range of animal hosts. The six species display distinct animal host preferences and have variable virulence in man. *B. abortus* infections are mostly associated with the disease in cattle, *B. melitensis* with small ruminants and camelids, *B. suis* with pigs, hares, rodents and rangifers (depending on biovar), *B. ovis* with sheep and *B. canis* with dogs. *B. neotomae* has only ever been reported in desert wood rats.

Diagnosis of *Brucella* infection can be achieved via Complement Fixation Test, Serum Agglutination Test, Rose Bengal antigen Test, and ELISA (Enzyme-Linked Immunosorbent Assay) methods. Routine surveillance for brucellosis is carried out in several countries using a simple indirect ELISA method. The antigen used in the ELISA is a crude preparation of *Brucella* LPS. The LPS of *Brucella* is the serodominant antigen associated with smooth strain infections of *Brucella*.

A number of vaccines are currently licensed for use in livestock against the various important pathogenic species of *Brucella*, all of which are live attenuated strains of the organism. *B. abortus* S19 and *B. abortus* RB51 vaccines have been used for the protection of cattle against brucellosis (for review see Cheville, 2000, Ann. NY Acad. Sci. 916: 147-153). S19 was developed through laboratory culture and selection of altered phenotypic characteristics when compared to the parent strain *B. abortus* 544. RB51 was similarly selected as a stable 'rough' mutant of *B. abortus* 2308. *B. suis* S2, a naturally occurring avirulent isolate of *B. suis* biovar 1, has been used extensively for the vaccination of pigs in China, where success rates are reportedly high. However, evaluation of this vaccine in other locations has resulted in extremely variable efficacy and its use has not been widely adopted.

The live attenuated vaccine *B. melitensis* Rev.1 has been established as recommended for the protection of sheep and goats against *B. melitensis* (Alton, 1987, Trop. Anim. Health Prod. 19: 65-74; Garin-Bastuji et al., 1998, Vet. Res. 29: 255-274) and is intermittently used as part of the control strategy in affected Mediterranean countries. Rev.1 was derived through laboratory culture and selection of altered phenotypic characteristics compared to the parent strain *B. melitensis*. There are currently no *Brucella* vaccines available for the prophylaxis of human infection.

The use of a live attenuated vaccine strain essentially involves the deliberate infection of the naïve animal with attenuated *Brucella* such that protective immune responses are elicited without concurrent pathology. The genetic mechanism underlying the attenuation of each of the vaccine strains is not fully understood.

Although there have been attempts to produce non-living vaccines, these have not been as widely accepted or successful as the live strains. One of the most widely studied non-living vaccines was the *B. abortus* 45/20 vaccine. An adjuvanted bacterin vaccine was reported to be protective in cattle and did not directly cause abortion. However, yearly boosters were required to maintain immunity, and local reactogenicity at the inoculation site was found to be a considerable problem. Furthermore, insufficient standardization in the production and evaluation methods for the killed preparations resulted in unacceptable levels of variability in efficacy between batches. Ultimately the use of the 45/20-adjuvant vaccine was abandoned in favor of the more consistent and longer-lived immunizing properties of the live vaccines such as S19. Numerous other attempts to generate non-living *Brucella* vaccines, either using simple bacterins or fractionated antigen preparations, have concluded that these preparations are poorly immunogenic.

Similarly, a number of recombinant protein based vaccines have been assessed but in each case these have been unable to promote comparable protective immunity to the live vaccines. A variety of delivery strategies have been employed for these recombinant antigens ranging from simple direct inoculation of the protein to formulation with adjuvants such as CpG ODN or delivery via vaccinia or *Escherichia coli*.

Recently a novel non-living vaccine based upon antigenic extracts of rough strain *B. ovis* has been described (Murillo et al., 2001, Vaccine 19: 4099-5106). The vaccine consists of hot saline extracted membrane antigens microencapsulated within poly-ϵ-caprolactone particles, and is able to protect rams against infection with *B. ovis*. However, at present there are not any non-living vaccines that are licensed for use against brucellosis, and none with reported efficacy against smooth strain *Brucella*.

We have previously reported on the development and in vitro assessment of five DNA vaccines encoding the genes omp25, FliC, FrpB, AcvB and invasion protein B ("iaIB", also known as "invB" and "iaiB") (Commander et al., 2003, Poster presentation at "*Brucellosis* 2003" Conference, Pamplona, Spain, September 15-17). It was demonstrated that mice receiving a naked DNA vaccine based upon either iaIB or omp25 were able to control infection by *B. melitensis* 16M to a similar level to those receiving the live attenuated vaccine Rev.1. The protective effect of the vaccines was seen using four intramuscular inoculations of 100 μg plasmid, given at three week intervals.

Numerous mechanical and formulation strategies have been investigated for ability to increase in vivo transfection efficiencies. Among the widely reported mechanical strategies for improving the delivery of DNA vaccine plasmids to host cells are ballistic devises referred to "Gene guns", and in vivo electroporation strategies. In addition to the mechanical strategies, the physical formulation of a vaccine can impact upon immunogenicity and efficacy. The formulation of vaccines with classical adjuvants such as alum, and oil and water emulsions are the most notable examples of this.

Vaccines such as *B. abortus* S19 and *B. melitensis* Rev.1 are live attenuated smooth strain infections and therefore induce LPS specific immune responses that cannot readily be distinguished from the immune response associated with a virulent infection. Differentiation of animals producing antibodies in response to LPS from vaccine strains or virulent strains is not possible using LPS-detection assays such as ELISA assays, resulting in vaccinated animals presenting as '*Brucella* positive' in serodiagnostic tests. The practical and political issues of differential diagnosis are an impediment to an effective vaccination-based control strategy. Since *Brucella* reactors have to be eliminated in order to maintain or obtain Officially Brucellosis Free ("OBF") status, prophylactic vaccination using for example the approved Rev.1 vaccine is incompatible with test and slaughter campaigns.

SUMMARY OF THE INVENTION

One object of the present invention is to improve the efficiency of vaccination using DNA vaccines based upon iaIB, for example by enhancing the immune response compared with a naked DNA vaccine based upon iaIB.

A further object of the present invention is to provide a means of distinguishing between vaccinated animals and *Brucella*-infected animals.

According to a first aspect of the present invention, there is provided an immunogenic nucleic acid composition comprising DNA encoding a polypeptide selected from the group consisting of: (i) *Brucella melitensis* Invasion Protein B (IaIB protein) having an amino acid sequence as shown in SEQ ID NO: 12; (ii) a polypeptide having at least 95% sequence identity to (i); and (iii) an immunologically active fragment of (i) or (ii), and an adjuvant, wherein said adjuvant is a liposome.

According to a further aspect of the invention, there is provided a DNA composition comprising a plasmid vector having DNA encoding a polypeptide selected from the group consisting of: (i) *Brucella melitensis* Invasion Protein B (SEQ ID NO: 12); (ii) a polypeptide having at least 95% sequence identity to (i); and (iii) an immunologically active fragment of (i) or (ii), in which said plasmid vector is adsorbed to a liposome.

The compositions of the invention, when administered to an animal subject, may induce an immune response that is characterized by enhancement of T cell priming and/or antibody generation compared with an immune response induced by a naked DNA vaccine encoding a polypeptide selected from the group consisting of: (i) *Brucella melitensis* Invasion Protein B (SEQ ID NO: 12); (ii) a polypeptide having at least 95% sequence identity to (i); and (iii) an immunologically active fragment of (i) or (ii).

The liposome is preferably a cationic liposome. DNA may be passively adsorbed to the liposome.

A further aspect of the invention provides a lipid-formulated vaccine comprising DNA encoding a polypeptide selected from the group consisting of: (i) *Brucella melitensis* Invasion Protein B (SEQ ID NO: 12); (ii) a polypeptide having at least 95% sequence identity to (i); and (iii) an immunologically active fragment of (i) or (ii).

The DNA of the invention may comprise the nucleotide sequence of SEQ ID NO: 11 which encodes the Invasion Protein B (IaIB). Alternatively, the DNA may comprise a nucleotide having at least 50, 55, 60, 65, 70, 75, 80, 85, 90, 95, 97 or 99% identity, for example 95% identity, to the nucleotide sequence of SEQ ID NO: 11. In another embodiment, the DNA of the composition may hybridize under high stringency conditions with the nucleotide defined by SEQ ID NO: 11.

The DNA of the invention in its various aspects may comprise a fragment of at least 15, 20, 25 or more nucleotides of SEQ ID NO: 11. Alternatively, the DNA of the invention may encode a polypeptide comprising the amino acid sequence of SEQ ID NO: 12. In another embodiment, the DNA of the invention encodes a fragment comprising at least 15 contiguous amino acids of SEQ ID NO: 12. A nucleic acid molecule complementary to the DNA molecules defined herein is also within the scope of the invention.

The DNA of the invention in its various aspects may encode a polypeptide having the amino acid sequence of SEQ ID NO: 12. Alternatively, the DNA may encode a polypeptide having at least 50, 55, 60, 65, 70, 75, 80, 85, 90, 95, 97 or 99% identity, for example 95% identity, to the polypeptide of SEQ ID NO: 12. An immunologically active fragment of either of these polypeptides is encompassed within the scope of the invention.

The DNA of the invention in its various aspects may encode Invasion Protein B (IaIB) from *Brucella melitensis* (for example, strain 16M, as shown in SEQ ID NO: 12) or other *Brucella* species such as *B. abortus* (for example, biovar 1), *B. suis* (for example, strain 1330) or other related *Brucella* species or strains referred to in the background section above. Sequence information for such *Brucella* polypeptides may be obtained for example in Genbank accession No. YP_221125.1 (*B. abortus* biovar 1 strain 9-941) and Genbank accession No. AE_014291.4 (translated nucleotides 349400-348878 of *B. suis* strain 1330 chromosome I), which are incorporated herein by reference.

Also provided according to the invention is a method of inducing an enhanced immune response to *Brucella* infection in an animal, comprising administering to said animal an effective amount of the composition or the vaccine as described herein, thereby inducing an enhanced immune response which is characterized in that it is greater in magnitude than an immune response induced by a naked DNA vaccine comprising DNA encoding a polypeptide selected from the group consisting of: (i) *Brucella melitensis* Invasion Protein B (SEQ ID NO: 12); (ii) a polypeptide having at least 95% sequence identity to (i); and (iii) an immunologically active fragment of (i) or (ii).

The enhanced immune response may be characterized by increased antibodies and/or enhanced T cell priming.

The method and or compositions may be useful for an animal selected from the group of: a mammal, a human, a ruminant, a sheep, a goat, a bison, a buffalo, an elk, a reindeer, and a caribou. In one embodiment, the animal excludes a pig.

The method of inducing an enhanced immune response may comprise multiple, preferentially sequential, administrations of an effective amount of the composition or the vaccine of the invention.

Another aspect of the present invention is a method for the differential diagnosis in an animal of brucellosis and vaccination by an immunogenic nucleic acid composition having DNA encoding a polypeptide selected from the group consisting of: (i) *Brucella melitensis* Invasion Protein B (SEQ ID NO: 12); (ii) a polypeptide having at least 95% sequence identity to (i); and (iii) an immunologically active fragment of (i) or (ii), comprising the steps of: (a) detecting the presence or absence of *Brucella* lipopolysaccharide (LPS) in said animal to ascertain whether or not said animal has a brucellosis infection; (b) detecting the presence or absence of said immunogenic nucleic acid composition in said animal to ascertain whether or not said animal has been vaccinated against brucellosis infection; and (c) correlating the results of steps (a) and (b) to determine whether or not said animal has a brucellosis infection and/or has been vaccinated against brucellosis.

In a further aspect of the invention there is provided a method for determining whether an animal free of brucellosis infection has been vaccinated by an immunogenic nucleic acid composition having DNA encoding a polypeptide selected from the group consisting of: (i) *Brucella melitensis* Invasion Protein B (SEQ ID NO: 12); (ii) a polypeptide having at least 95% sequence identity to (i); and (iii) an immunologically active fragment of (i) or (ii), comprising the steps of: (a) detecting the presence or absence of *Brucella* lipopolysaccharide (LPS) in said animal to ascertain whether or not said animal has a brucellosis infection; (b) detecting the presence or absence of said immunogenic nucleic acid composition in said animal to ascertain whether or not said animal has been vaccinated against brucellosis infection; and (c) correlating the results of steps (a) and (b) to determine whether or not said animal free of brucellosis infection has been vaccinated with said composition.

Steps (a) and/or (b) of the above method may be performed on serum obtained from said animal using an ELISA-based assay (examples of which are provided below).

In these methods, the DNA and its encoded protein may have a sequence as described above, for example with respect to SEQ ID NO: 11 and SEQ ID NO: 12, respectively.

In another aspect of the invention there is provided a kit comprising: (a) a means for detecting brucellosis infection in an animal; and (b) a means for detecting vaccination of said animal by an immunogenic nucleic acid composition having DNA encoding a polypeptide selected from the group consisting of: (i) *Brucella melitensis* Invasion Protein B (SEQ ID NO: 12); (ii) a polypeptide having at least 95% sequence identity to (i); and (iii) an immunologically active fragment of (i) or (ii).

Either or both of the means may be ELISA-based.

The invention also envisages a method of conferring immunity against brucellosis to an animal using a non-living vaccine, in which said immunity is induced primarily by a major histocompatibility complex (MHC) class 11-derived immune response comprising the step of inoculating said animal with an immunogenic nucleic acid composition having DNA encoding a polypeptide selected from the group consisting of: (i) *Brucella melitensis* Invasion Protein B (SEQ ID NO: 12); (ii) a polypeptide having at least 95% sequence identity to (i); and (iii) an immunologically active fragment of (i) or (ii).

The said immunity may be additionally conferred by a protective antibody production against brucellosis resulting from said step of inoculating. The antibodies may comprise IgG1 and IgG2a antibodies, for example in a balanced ratio of about 0.75:1 to about 1:0.75.

The said nucleic acid composition in these aspects is preferably a naked DNA composition.

Also provided is a method of conferring immunity against brucellosis to an animal using a non-living vaccine, in which said immunity is characterized by preferential activation of helper ($CD4^+$) T cells effective against brucellosis over cytotoxic and/or suppressor ($CD8^+$) T cells effective against brucellosis, comprising the step of inoculating said animal with an immunogenic nucleic acid composition having DNA encoding a polypeptide selected from the group consisting of: (i) *Brucella melitensis* Invasion Protein B (SEQ ID NO: 12); (ii) a polypeptide having at least 95% sequence identity to (i); and (iii) an immunologically active fragment of (i) or (ii).

Further provided is a method of inducing in an animal a helper ($CD4^+$) T cell-mediated response effective against brucellosis in preference to a cytotoxic and/or suppressor ($CD8^+$) T cell-mediated response effective against brucellosis using a non-living vaccine, comprising administering to said animal an effective amount of an immunogenic nucleic acid composition having DNA encoding a polypeptide selected from the group consisting of: (i) *Brucella melitensis* Invasion Protein B (SEQ ID NO: 12); (ii) a polypeptide having at least 95% sequence identity to (i); and (iii) an immunologically active fragment of (i) or (ii).

The invention encompasses in another aspect a method of inducing in an animal an immune response characterized by preferential activation of helper ($CD4^+$) T cells effective against brucellosis over cytotoxic and suppressor ($CD8^+$) T cells effective against brucellosis using a non-living vaccine, comprising the step of inoculating said animal with an immunogenic nucleic acid composition having DNA encoding a polypeptide selected from the group consisting of: (i) *Brucella melitensis* Invasion Protein B (SEQ ID NO: 12); (ii) a polypeptide having at least 95% sequence identity to (i); and (iii) an immunologically active fragment of (i) or (ii).

The said immune response may further include production of antibodies against *Brucella melitensis* Invasion Protein B or an immunologically active fragment thereof.

The said immune response may provide protection against brucellosis infection.

The composition or vaccine of the present invention may be administered in more than one dose, for example at least three to four doses. The doses may be at intervals of 7 to 21 days.

DETAILED DESCRIPTION OF THE INVENTION

Figure 1:
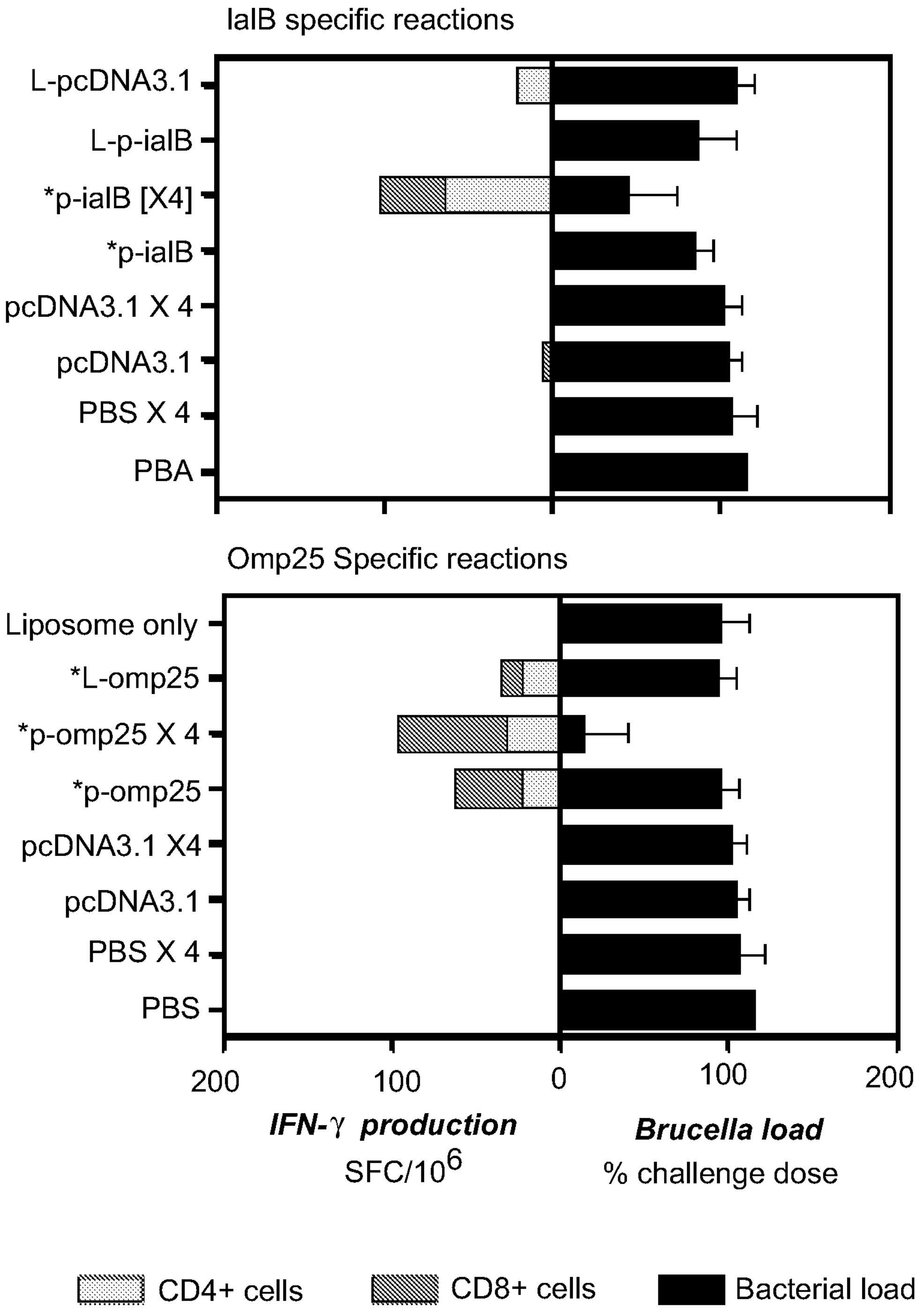
FIG. 1 is a graphical representation of the relationship between the protective efficacy of vaccination and the generation of antigen specific IFN-γ secreting effector cells.

The present application describes a composition and method for vaccination against and differential diagnosis of brucellosis infection caused by *Brucella* species. The composition in one aspect is a DNA composition adhered to a liposome, which we have found improves immune response compared to a naked DNA composition.

DNA vaccination involves administering antigen-encoding polynucleotides in vivo to induce the production of an immunologically active antigen within the target cells. The introduction of the DNA vaccine generally leads to the expression within those cells of the structural protein determinants associated with the pathogen protein or proteins. The proteins are cleaved by antigen processing mechanisms of the host to form peptide fragments which will be displayed on the cellular surface of the transfected cells in conjunction with the Major Histocompatibility Complex (MHC) antigens of the normal cell. Even when cell-mediated immunity is not the primary means of preventing infection, it is likely important for resolving established infections. Furthermore, the structural proteins released by the expressing transfected cells may also be recognized by Fc receptors or processed as exogenous antigens in order to trigger systemic humoral antibody responses. Details of responses effected by the present vaccines are described elsewhere in this application.

The DNA encoding the desired antigen may be introduced into the cell in any suitable form including, a linearized plasmid, a circular plasmid, a plasmid capable of replication, an episome, RNA, etc. Preferably, the gene is contained in a plasmid. In a particularly preferred embodiment, the plasmid is an expression vector. Individual expression vectors capable of expressing the genetic material may be produced using standard recombinant techniques. See for example Maniatis et al., 1985, Molecular Cloning: A Laboratory Manual, Cold Spring Harbor Laboratory Press, or DNA Cloning, Vol. I and II (D. N. Glover, ed., 1985) for general cloning methods.

Preferably, a promoter sequence operable in the target cell is operably linked to the DNA sequence of the vaccine. Several such promoters are known for mammalian systems which may be joined 5', or upstream, of the coding sequence for the encoded protein to be expressed. A suitable promoter is the human cytomegalovirus immediate early promoter. A downstream transcriptional terminator, or polyadenylation sequence, such as the polyA addition sequence of the bovine growth hormone gene, may also be added 3' to the protein coding sequence.

In one aspect of the invention, the DNA vaccine is bound (or adsorbed) to a liposome. Liposomes are generally produced from phospholipids or other lipid substances. They may have one bilayer (unilamellar) or two or more bilayers (multilamellar). A liposome in solution is generally in the shape of a spherical vesicle having one or several concentric layers of lipid molecules each of which is represented by the formula XY wherein X is a lipophobic-hydrophilic moiety and Y is a lipophilic-hydrophobic moiety. In solution, the concentric layers are arranged such that the hydrophilic moiety remains in contact with an aqueous phase.

Liposomes within the present invention may be prepared in accordance with known laboratory techniques. In one embodiment, liposomes may be made according to the method of Brewer et al. (1998, J. Immunol. 161: 4000-4007). In the alternative, liposomes may be prepared in accordance with other known laboratory procedures. Any lipid capable of forming vesicles may be employed. For clinical application, it is desirable that the lipid be non-toxic, physiologically acceptable, and metabolizable. Common bilayer forming lipids having clinical potential are phospholipids, fatty acids, sphingolipids, glycosphingolipids, and steroids. Glycerol containing phospholipids are the most commonly used component of liposome formulations having clinical utility. One commonly used example is phosphatidylcholine or lecithin. The steroid cholesterol and its derivatives are often included as components of liposomal membranes. The tendency of liposomes to aggregate and fuse can be controlled by the inclusion of small amounts of acidic or basic lipids in the formulation. The properties of liposomes containing phospholipids are determined by the chemistry of the phospholipid. Important considerations are the hydrocarbon chain length, degree of unsaturation of the hydrocarbon chain, degree of branching of the hydrocarbon chain, and temperature of the system.

Multilamellar liposomes may be created by depositing a mixture of lipids as a thin film by evaporation under reduced pressure followed by dispersion with an excess volume of aqueous buffer containing the antigen with or without organic solvents. Another method is to mix the aqueous phase containing the DNA with small unilamellar liposomes followed by lyophilization. The multilamellar liposomes are formed when the lyophilized product is rehydrated, usually with a small amount of distilled water. The small unilamellar liposomes to be used in this process may be produced by dispersing the lipids in an aqueous medium followed by a mechanical means of dispersion such as sonication, use of a high pressure device, or a solvent injection method. Large and intermediate sized unilamellar liposomes may also be produced by conventional techniques including detergent dialysis, extrusion through small pore size membranes under high pressure, freeze thawing followed by slow swelling, dehydration followed by rehydration and dilution, or dialysis of lipids in the presence of chaotropic ions. The size of the liposomes may be made more uniform by fractionation procedures such as centrifugation or size exclusion chromatography, homogenization, or capillary pore membrane extrusion.

Other adjuvants well known in the art may be included in vaccine compositions of the present invention. Examples of conventional adjuvant which may be used include: aluminum compounds, also known as aluminum gel, such as aluminum hydroxide, $Al(OH)_3$ and aluminum phosphate, $AlPO_4$; potassium aluminum sulfate; Freund's complete adjuvant ("FCA"); Freund's incomplete adjuvant ("FIA"); water-in-oil emulsion; oil-in-water emulsion; and the like.

Furthermore, as is usual in the prior art, different doses of the vaccine compositions may be tested to determine optimal regimes for a particular human or animal patient group. For example, the size of the animal or human is a factor to be taken into account to determine dosage amount and regime.

As used herein, the term "enhanced immune response" indicates in one aspect an immune response induced by a composition of the invention which response is characterized by a greater humoral (i.e. antibody-based) response and/or a greater cell-mediated (for example, T cell) response relative to an immune response induced in the absence of said composition. The enhanced response may be characterized by an increase in the number and/or effectiveness of agents involved in the immune response (for example, antibodies and/or T cells). The immune response may be quantified as provided by way of example in the specific embodiments below. Alternative methods of quantifying agents involved in an immune response are well known to skilled artisans and are included herein by reference.

Sequence identity or similarity between amino acid sequences or between nucleotide sequences may be determined by comparing an alignment of the sequences. When an equivalent position in the compared sequences is occupied by the same base or amino acid, then the molecules are identical at that position. Scoring an alignment as a percentage of identity is a function of the number of identical amino acids or bases at positions shared by the compared sequences.

When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

Suitable computer programs for carrying out sequence comparisons are widely available in the commercial and public sector. Examples include the Gap program (Needleman & Wunsch, 1970, *J. Mol. Biol.* 48: 443-453) and the FASTA program (Altschul et al., 1990, *J. Mol. Biol.* 215: 403-410). Gap and FASTA are available as part of the Accelrys GCG Package Version 11.1 (Accelrys, Cambridge, UK), formerly known as the GCG Wisconsin Package. The FASTA program can alternatively be accessed publically from the European Bioinformatics Institute (http://www.ebi.ac.uk/fasta) and the University of Virginia (http://fasta.biotech.virginia.edu/fasta_www/cgi). FASTA may be used to search a sequence database with a given sequence or to compare two given sequences (see http://fasta.bioch.virginia.edu/fasta_www/cgi/search_frm2.cgi). Typically, default parameters set by the computer programs should be used when comparing sequences. The default parameters may change depending on the type and length of sequences being compared. A sequence comparison using the FASTA program may use default parameters of Ktup=2, Scoring matrix=Blosum50, gap=−10 and ext=−2.

Sequences of the present invention may be identified in that they hybridize with the sequence of SEQ ID NO: 11 under stringent hybridization conditions. Such conditions would be well understood by the person skilled in the art, and are exemplified for example in Sambrook et al. (1989; Molecular Cloning: A Laboratory Manual, Cold Spring Harbor Laboratory Press). In general terms, high stringency conditions as 0.1×SSC at about 65° C. SSC (standard saline-citrate, pH about 7.0) is a buffer consisting of 0.15 M NaCl and 0.015 M trisodium citrate, with 0.1×SSC being 10% of the strength of the standard buffer.

The present invention will now be described in more detail by way of the following non-limiting examples, with reference to the accompanying drawings.

EXAMPLE 1

Characterisation of Two Protective DNA Vaccines Against Brucellosis

In first example we describe the characterization of two DNA vaccines based upon the *B. melitensis* 16M genes ialB and omp25. Example 1 in part includes data previously described in Commander et al. (2003, supra).

Materials and Methods

Candidate Selection:

In silico candidate selection was supported by the confirmation of transcription of the specific gene in cultured *B. melitensis* 16M, and the detection of candidate specific antibody responses in experimentally infected sheep.

Construction of and In Vitro Assessment of DNA Vaccine Plasmids PCR and Cloning:

Selected genes were amplified by PCR for cloning into eukaryotic expression vectors (primer details and PCR conditions are provided in Tables 1 and 2). All reactions were carried out using a Progene™ Thermal cycler (Techne, Minneapolis, Minn., USA). Purified PCR products were ligated with the pCR3.1™ vector (Invitrogen Ltd, Paisley, UK), and identity of constructs was confirmed by restriction analysis and sequencing. Sequencing reactions were performed by Oswel Laboratories (Oswel, Southampton, UK).

TABLE 1

Primers used for the amplification of Brucella-specific genes.

| Target gene | Primer details (all shown in 5′-3′ orientation) |
|---|---|
| omp25 | Forward primer: AAACTCGAGCCGCCACCATGCGCACTCTTAAGTCT (SEQ ID NO: 1)<br>Reverse primer: AAATCTAGAACCGGATGCCTGAAATCCTT (SEQ ID NO: 2) |
| ialB | Forward primer: AAAGGATCCGCCACCATGAAAAATTATCGTG (SEQ ID NO: 3)<br>Reverse primer: AAAGAATTCTTACTTGGTCAATGCCTGAAT (SEQ ID NO: 4) |
| omp25* | Forward primer: TGCGCAACTCTTAAGTCTCTT (SEQ ID NO: 5)<br>Reverse primer: TTAGAACTTGTAGCCGATGCC (SEQ ID NO: 6) |
| IF-1* | Forward primer: ATGGCGAAAGAAGAAGTCCT (SEQ ID NO: 7)<br>Reverse primer: ACTAGAACCTTGTCACCGGC (SEQ ID NO: 8; Eskra et al., 2001, Infect. Immunol. 69: 7736-7742) |

Restriction enzyme sites boxed
Kozac sequence underlined
*primers used only for RT-PCR investigations (not cloning)

TABLE 2

Optimized PCR conditions for cloning, using genomic DNA from *B. melitensis* 16M as template.

| Gene identity | PCR details |
|---|---|
| omp25 | Total volume: 100 μl.<br>Template: 20 μl *B. melitensis* 16M genomic DNA @ 200 μg/ml.<br>Reaction conditions: Perkin Elmer PCR system: X1 PCR Buffer II, 1.5 mM $MgCl_2$, 1.0 mM dNTPs, 200 nM ea. Primer, 10% glycerol, 5U Taq<br>Cycling conditions:<br>1 [95° C. × 5 min, 58° C. × 2 min, 70° C. × 3 min]<br>30 [95° C. × 1 min, 58° C. × 2 min, 70° C. × 3 min]<br>1 [95° C. × 1 min, 58° C. × 2 min, 70° C. × 12 min]<br>Product size: 750 bp |
| ialB | Total volume: 50 μl<br>Template: 5 μl *B. melitensis* 16M genomic DNA @ 200 μg/ml.<br>Reaction conditions: Perkin Elmer PCR system: X1 PCR Buffer II, 10% glycerol, 3.0 mM $MgCl_2$, 2.5 mM dNTPs, 200 nM ea. Primer, 5U Taq<br>Cycling conditions:<br>1 [94° C. × 5 min]<br>35 [95° C. × 90 sec, 56° C. × 90 sec, 72° C. × 120 sec]<br>1 [72° C. × 12 min]<br>Product size: 546 bp |

In Vitro Evaluation of Vaccine Expression:

The in vitro expression of the encoded gene from the vaccine construct was assessed following transfection of Cos7 cells and candidate specific reverse transcriptase PCR (RT-PCR).

Transfection:

Lipofectamine™ Plus™ transfection procedures (Invitrogen Ltd, Paisley, UK) were used in transfection experiments. Briefly, endotoxin free construct DNA was diluted to 10 μg/ml in serum and antibiotic free Modified Eagles Media (MEM), and mixed in a 1:1 ratio with serum and antibiotic free MEM supplemented with 20% Lipofectamine™ transfection agent and 2% Plus™ reagent. The mixture was incubated for 30 minutes at RT to allow formation of DNA: Lipofectamine complexes. Cos7 monolayer cultures, in 12-well plates, at between 40-80% confluence were washed three times in serum and antibiotic free Modified Eagles Media (MEM). After washing, each well was replenished with 0.4 ml of serum and antibiotic free MEM to which 100 μl of transfection mixture was added. Plates were incubated at 37° C., 5% $CO_2$ for 12 hours, to promote uptake of the transfection particles. After uptake, media was supplemented with serum and antibiotics, by the addition of 0.5 ml MEM, containing 20% v/v Fetal Bovine Serum and 2% v/v Antibiotic Antimycotic solution (Stock solution: 10,000 U/ml Penicillin, 100 mg/ml Streptomycin, 25 mg/ml Amphotericin B). Cultures were then further incubated at 37° C., 5% $CO_2$ for 24 hours prior to RNA harvest.

RNA Harvest and cDNA Production:

Total RNA was harvested from the cell cultures using Tri-Reagent™ protocols as per manufacturer's instructions. Briefly, transfected Cos7 cultures were washed 3× with sterile PBS. 1.0 ml of Tri-Reagent™ (Sigma, Poole, UK) was added to each well, and monolayers were disrupted by scraping with a pipette tip and vortexing. The cell: tri-reagent suspension (1 ml) was transferred to microfuge tubes, and vortexed for a further 10 minutes. 0.2 ml of Chloroform (Molecular Biology Grade Reagent) (Sigma, Poole UK) was added to each tube. These samples were vortexed briefly and then incubated on ice for 5 minutes. Samples were centrifuged at 10,000×g at 4° C. for 10 minutes, for phase separation. The RNA present in the aqueous phase was precipitated by addition of 0.5 ml of Isopropanol (Molecular Biology Grade Reagent), brief vortexing and incubation on ice for 20 minutes before centrifuging (10,000×g for 20 minutes at 4° C. Precipitated RNA was washed twice in 75% ethanol by centrifugation (10 minutes, 10,000×g, 4° C.), and the pellets air dried for 20 minutes, before resuspension in 20 μl of DEPC treated water.

Genomic DNA Removal from Total RNA Samples:

All samples were treated with Ambion DNA-Free™ (Ambion, Austin, Tex., USA), according to manufacturers instructions, to remove traces of genomic DNA. Briefly, 5 μl of DNAse1 was added to each 20 μl aliquot of RNA, and incubated at 37° C. in a water bath for 30 minutes. 10 μl of DNase removal agent was added to each tube and mixed using a Denley rotary cell mixer for 10 minutes, before centrifuging (10,000×g, 4° C., for 1 minute, Hereaus Biofuge Fresco) to sediment the removal reagent. Supernatant was transferred to a clean labeled sterile tube, and used immediately in cDNA production or frozen at −80° C. until use.

Reverse Transcription of Transfected Cos7 Cell Derived Total RNA to Generate cDNA:

cDNA production was performed using the reagents supplied with the Ambion Retroscript™ RT-PCR kit (Ambion, Austin, Tex., USA). For each RNA sample, Oligo-dT™ primers were used to prime the reaction for reverse transcription. 2 μl of Oligo-dT™ primer was added to 12 μl of the relevant RNA sample. The sample was then heated to 82° C. for 3 minutes. Remaining reagents for RT-PCR added on ice to a final concentration of 2 mM dNTPs, 5 IU M-MLV-RT enzyme, 5 IU of Superasin™ RNAse inhibitor in X1 Retroscript™ buffer Reverse transcription reaction was incubated at 42° C. in the Techne™ Progene™ Thermal cycler (Techne, Minneapolis, Minn., USA) for 90 minutes, and then heated to 80° C. for 10 minutes to stop the reaction. The cDNA was used immediately in specific PCR reactions or stored at −80° C. in 5 μl aliquots until required.

For PCR from cDNA templates from Cos 7 RNA, the Accuprime™ system was used (Invitrogen, Paisley, UK). Accuprime reagents provided a complete PCR mastermix, to which the primers at an appropriate concentration (0.2 nM), and the template cDNA samples were added. 2-5 μl of template cDNA was used in each reaction. Reactions were set up in 50 μl total volumes, with 25 μl of the Accuprime I™ reagent, 1 μl of each primer at 0.2 nM concentration, and 19-22 μl of DEPC treated water. Each reaction involved an initial denaturation and enzyme activation step at 94° C. for 5 minutes, followed by 20 cycles of denaturation at 94° C. for 30 seconds, annealing at 58.5° C. for 30 seconds, and extension at 72° C. for 30 seconds. A final prolonged extension step for 5 minutes concluded the reaction.

For Production of Inocula:

Three day old SDA cultures were harvested into 0.1 M sterile PBS, and adjusted to appropriate CFU concentrations using nephelometry. Mice were inoculated within one hour of inocula preparation, and exact CFU doses calculated retrospectively, through serial dilution and culture on SDA.

Immunogenicity of Selected Antigens in Target Species:

Recombinant proteins were generated for each of the selected antigens. Briefly, the gene of interest was subcloned from the DNA vaccine constructs into inducible prokaryotic expression vectors encoding N terminal fusion tags pGEX-6P (Amersham, Bucks, UK), or pRSET (Invitrogen, Paisley, UK). Expression was determined through demonstration of an appropriate sized protein in bacterial lysate separated by SDS-PAGE (BioRad Protean II mini-gel system (Bio-Rad, Herts, UK), 12.5% acrylamide gel), and immunodetection of the fusion tag following western blotting (data not shown). Culture conditions were optimized for maximal expression and bacterial lysate harvested for use in ELISA.

For ELISA, individual lysates were coated to polystyrene plates (Polysorp, Nunc-brand, Fischer Scientific, UK) at a total protein concentration of 50 μg/ml. Lysate from *E. coli* pGEX-6P expressing GST alone or pRSET expressing Histidine tagged porcine IFNμ were used as controls. Coated plates were incubated at 4° C. overnight, prior to blocking. Plates were washed twice with 0.1M PBS 0.05% Tween 20 (PBS-T), and incubated with blocking buffer (4% dried skimmed milk powder, 0.1M PBS 0.5M EDTA) supplemented with Rabbit anti-*E. coli* immunoglobulins (0.025%) (Dako, DakoCytomation, Denmark), for 2 hours at 25° C. Plates were washed four times with PBS-T and test sera (1/200 in diluent buffer: 1% dried skimmed milk, 0.1M PBS, 0.5M EDTA), from 23 experimentally infected sheep and 5 uninfected controls, applied. Test serum was incubated at 37° C. for one hour. Plates were washed six times in PBS-T prior to the application of anti-sheep IgG horse-radish peroxidase conjugate (Amersham, Bucks, UK) (1/4000 in diluent buffer). Plates were incubated for one hour at 37° C. Plates were washed six times with PBS-T, and blotted dry prior to incubation with TMB (3'3'5'5' Tetramethylbenzidine) substrate (Vetoquinol, Bicester, UK) for 30 minutes at 25° C. in the dark. The reaction was stopped by addition of 0.1M citric acid, and read immediately using a Titertek Multiscan II to determine optical density at 450 nm.

All sera were tested for reactivity against each of the recombinant antigen preparations including the controls, and also in standard *Brucella* indirect ELISA ("iELISA") to confirm positive or negative status. An additional ELISA using Brucellergene™ (Synbiotics Corps, Merial, France) antigen: an LPS free preparation of *B. melitensis* B115 cytosolic proteins, at 45 μg/ml, was also conducted to the same general protocol.

Assessment of Protective Efficacy and Immunogenicity of Novel DNA Vaccines

Preparation of DNA for inoculation: Qiagen EndoFree™ plasmid Giga-Prep (Qiagen UK, Sussex, UK) methods were used to generate sufficient DNA for in vivo and in vitro evaluations. Each DNA prep was checked for sequence identity and endotoxin content prior to use. Plasmid samples were sequenced by Oswel Sequencing Laboratories, Southampton, UK. Endotoxin content was determined by E-toxate™ (Sigma, Poole, UK), LAL assay. Preparations were considered suitable when shown to contain less than 1 endotoxin unit per ml. Where plasmids were obtained from a commercial source (PlasmidFactory, UK), they are certified free of LPS and endotoxin.

Inoculation and Challenge Procedures:

A BALB/c model of murine brucellosis was used for evaluation of vaccine immunogenicity and protective efficacy. Two similar studies were performed. In each study, female mice (6-8 weeks old, from Charles River Inc.) were divided into groups of five mice each. Groups 1-3 were inoculated intramuscularly with a total of 400 μg DNA per mouse: 4×100 μg per mouse, given at three week intervals (50 μl volume delivered to each quadriceps). (Group 1: p-omp25, 2: p-ialB, 3: pcDNA3.1). Group 4 received an equivalent volume and schedule of 0.1 M sterile PBS.

The inoculations were given at weeks zero, three, six and nine of the study.

Inoculations were delivered using a 0.5 ml 27 G×1¼ tuberculin syringe; the needle was sheathed by 0.56 μM diameter tubing, leaving only 4 mm of needle free for inoculation to ensure precise intramuscular delivery.

Group 5 was inoculated sub-cutaneously with approximately $2\times10^5$ CFU *B. melitensis* vaccine strain Rev.1 at week nine.

Thirty days later all mice were challenged with *B. melitensis* 16M. In challenge study A, mice received approximately $1\times10^4$ CFU *B. melitensis* 16M. In study B, mice received approximately $1\times10^6$ CFU *B. melitensis* 16M. All challenge inoculations were given intra-peritoneally. Mice were sacrificed at 15 days post-challenge, and the *Brucella* load of the spleen was determined. CFU data were normalized by log transformation and analyzed by one-way ANOVA with Dunnett's post-test, using the software associated with GraphPad Prizm4 software (GraphPad Inc, Calif., USA).

Serological Response Measurement

To determine the ability of the vaccines to induce *Brucella* specific immune responses, sera were collected from mice two weeks after completion of the vaccination schedule. These sera were assayed for the presence of *Brucella* specific IgM, IgG1 and IgG2a (using whole *B. melitensis* 16M as antigen). Briefly, killed 16M antigen was prepared coated to Maxisorp™ 96 well plates (Nunc) at 4° C. overnight. Plates were washed twice with PBS-T wash buffer and 200 μl per well of blocking solution (4% skimmed milk powder (Marvel) in PBS-EDTA buffer) was added to the plates, which were incubated at RT for ≥2 hours.

After blocking, plates were washed once in PBS-T wash buffer and the test serum and controls (diluted 1:100 in 1% marvel PBS-EDTA diluent) applied to the plate. Normal mouse serum (Sigma, Poole, UK) was used as a negative control in these ELISAs. Positive control serum was obtained from mice that had been infected with *B. melitensis* 16M in previous research projects at VLA Weybridge: The serum was collected from ten *B. melitensis* 16M infected mice at day 84 post-infection and pooled for use as a positive control. Plates were incubated at 37° C. for 90±10 minutes. Plates were then washed five times with PBS-T. Isotype specific anti-mouse Ig enzyme conjugated reagents were used as detection antibodies. Rat anti-mouse IgM (μ chain specific) peroxidase conjugated antibody at 1 in 2000 in diluent buffer, Goat anti-mouse IgG1 peroxidase conjugated antibody (STAIR P, Serotec, Oxford, UK) at 1 in 1000 in diluent buffer, and Goat anti-mouse IgG2a peroxidase conjugated antibody (STAR82P, Serotec, Oxford, UK) at 1 in 1000 in diluent buffer were used. These were incubated at 37° C. for 1 hour. Plates were washed 5 times with PBS-T and blotted dry onto absorbent matting. TMB (Vetoquinol, Bicester, UK) working solution was added to the plates and incubated for 10-30 minutes in the dark for reaction development. Reaction development was judged by eye, and when the IgG2a positive control wells had achieved sufficient intensity of color, the reaction was stopped by the addition of 100 μl per well of 0.1 M Citric acid solution. Plates were read within 1 hour of reaction completion using a Titertek Multiscan II to determine optical density at 450 nm.

For iELISA the CO for positive reactions was 10% of the OD of the standard positive control sera. For each of the individual recombinant protein ELISAs and the Brucellergene™ ELISA the CO was determined as the mean OD achieved from the five uninfected control sera. For test samples OD readings of greater than or equal to the CO were determined as positive, readings below the CO were classed as negative.

*Brucella* Specific Recall Cytokine Responses

Experiments were set up to measure basic cell mediated immune effectors induced by vaccines p-omp25 or p-ialB. Inoculation was conducted as described above, and spleens were harvested (n=3 per group) into prewarmed DMEM at intervals during the course of vaccination and at 12 weeks post-vaccination. Spleens were macerated and sieved to release splenocytes and remove debris, and reconstituted to $5\times10^6$ cells/ml in DMEM. Splenocyte suspensions were plated into 24 well tissue culture plates, mixed in a 1:1 ratio with stimulating antigens or controls, such that each well contained 2 ml volume of culture material, at $2.5\times10^6$ cells per ml. Negative stimulation controls consisted of cells in DMEM complete only. Concanavalin A (Sigma, Poole, UK) (5 μg/ml final concentration) was used as a mitogen control. *B. melitensis* 16M killed antigen (40 μg/ml) and Brucellergene™ (Synbiotics Corps, Merial, France) (40 μg/ml) were used to stimulate for *Brucella* specific responses. IFNγ, TNFα, IL-4 and IL-10 were measured in the supernatants (SNs) of cultured cells at 48 hours post-stimulation, using commercially available cytokine ELISAs (BioSource Europe, Belgium). ELISAs were carried out according to manufacturer's instructions. SN's were assayed in duplicate, neat and diluted 1:1 in sample diluent buffer. The concentration of each cytokine was estimated via comparison against known standards. Induced cytokine was determined through subtraction of the resting concentration (unstimulated samples) from the stimulated samples. Group average concentrations of induced cytokine were calculated as mean±standard deviation (n=3), and data was analyzed using the Mann-Whitney non parametric analysis (GraphPad Prizm4).

Results

Evidence of Transcription of the Candidate Genes in *Brucella*

RNA isolated from *Brucella* cultured on SDA, in Albimi broth or infecting murine splenocytes was assessed for the presence of candidate specific transcripts. Transcription of IF-1 was confirmed in all samples. Transcription of each candidate gene was measured under at least one of the conditions described. For omp25, iaIB and IF-1, specific transcripts were consistently evident under all three conditions.

Evidence of Candidate Antigen Immunogenicity in Target Species

Evidence of antibody responses to the crude cell lysates was obtained for all recombinant lysate preparations investigated. Control lysate ELISAs were used to demonstrate that reactivity in each of the sera was not a result of antibodies against abundant *E. coli* antigens or the fusion tags. In addition, *Brucella* iELISA and Brucellergene™ ELISA was used to confirm seropositivity in the sera of known infected animals and lack of *Brucella* specific antibodies in the uninfected samples. Data indicated that 91% and 76% of the infected sheep contained antibodies reactive in the Omp25 and iaIB ELISAs respectively. This reactivity was preserved when purified samples of these recombinant proteins were used as antigens in ELISA (data not shown). Results are shown in Table 3.

TABLE 3

Results from ELISAs to determine natural reactivity of *Brucella* infected sheep to the selected candidate antigens.

| | Recombinant candidate antigens | | | | | Controls | | Native antigens | |
|---|---|---|---|---|---|---|---|---|---|
| Sample ID | GST-Omp25 | GST-IalB | His-AcvB | His-FrpB | His-FliC | GST | His-Po.IFNγ | −S-LPS Bru | +S-LPS iELISA |
| Bru+ | + | + | − | + | − | − | − | + | + |
| Bru− | − | − | − | − | − | − | − | − | − |
| 3 | + | + | + | − | − | − | − | + | + |
| 4 | + | + | − | + | + | − | − | + | + |
| 5 | + | + | + | + | + | − | − | + | + |
| 6 | + | + | + | − | − | − | − | + | + |
| 7 | + | − | + | + | + | − | − | + | + |
| 10 | + | + | − | + | − | − | − | + | + |
| 12 | + | + | − | − | − | − | − | + | + |
| 14 | + | + | − | − | + | − | − | + | + |
| 16 | + | + | − | − | + | − | − | + | + |
| 18 | + | + | + | − | − | − | − | + | + |
| 24 | + | − | − | − | + | − | − | + | + |
| 25 | + | − | + | − | + | − | − | + | + |
| 26 | + | + | − | − | − | − | − | + | + |
| 27 | + | − | − | + | − | − | − | + | + |
| 29 | + | + | + | − | + | − | − | + | + |
| 30 | + | − | − | + | + | − | − | + | + |
| 33 | + | + | + | − | + | − | − | + | + |
| 34 | − | + | − | − | + | − | − | − | + |
| 35 | + | + | + | + | + | − | − | + | + |
| 36 | + | + | − | + | − | − | − | + | + |
| 38 | − | − | − | + | − | − | − | − | + |
| 39 | + | + | + | + | + | − | − | + | + |
| | 91% | 76% | 45% | 45% | 59% | 0% | 0% | 91% | 100% |
| 1 | − | − | − | − | − | − | − | − | − |
| 8 | − | − | − | − | + | − | − | − | − |
| 9 | − | − | − | − | − | − | − | − | − |
| 17 | − | − | − | − | − | − | − | − | − |
| 31 | − | − | − | − | + | − | − | − | − |
| | 100% | 100% | 100% | 100% | 80% | 100% | 100% | 100% | 100% |

Table 3 indicates the result determined from the each serum sample assayed at 1/200 dilution in each ELISA test. The CO for defining positivity was determined from the mean OD value of five known negative sera in each of the individual ELISAs. Samples with a mean OD > CO are indicated +,samples determined as negative (mean OD < CO) are indicated −. CO values for each ELISA are Omp25 = 0.652, laiB = 0.089, fliC = 0.340, acvB = 0.51, frpB = 0.663. The fliC, acvB and frpB antigens are alternative *Brucella* antigens originally selected for screening, and are not discussed in detailherein.

Amplification of omp25 and iaIB Genes

Using primers and conditions described in Tables 1 and 2 above, the opm25 gene sequence amplified from *B. melitensis* 16M genomic DNA (excluding flanking restriction sites added by primers) was:

```
                                                  (SEQ ID NO: 9)
  1 ATGCGCACTC TTAAGTCTCT CGTAATCGTC TCGGCTGCGT
    TGCTGCCGTT CTCTGCGACC

 61 GCTTTTGCTG CCGACGCCAT CCAGGAACAG CCTCCGGTTC
    CGGCTCCGGT TGAAGTAGCT

121 CCCCAGTATA GCTGGGCTGG TGGCTATACC GGTCTTTACC
    TTGGCTACGG CTGGAACAAG

181 GCCAAGACCA GCACCGTTGG CAGCATCAAG CCTGACGATT
    GGAAGGCTGG CGCCTTTGCT

241 GGCTGGAACT TCCAGCAGGA CCAGATCGTA TACGGTGTTG
    AAGGTGATGC AGGTTATTCC
```

-continued

```
301 TGGGCCAAGA AGTCCAAGGA CGGCCTGGAA GTCAAGCAGG
    GCTTTGAAGG CTCGCTGCGT

361 GCCCGCGTTG GCTACGACCT GAACCCGGTT ATGCCGTACC
    TCACGGCTGG TATTGCCGGT

421 TCGCAGATCA AGCTTAACAA CGGCTTGGAC GACGAAAGCA
    AGTTCCGCGT GGGTTGGACG

481 GCTGGTGCCG GTCTCGAAGC CAAGCTGACG GACAACATCC
    TCGGCCGCGT TGAGTACCGT

541 TACACCCAGT ACGGCAACAA GAACTATGAT CTGGCCGGTA
    CGACTGTTCG CAACAAGCTG

601 GACACGCAGG ATTTCCGCGT CGGCATCGGC TACAAGTTCT
    AATTATAGCA TAATTGGACA

661 CGGAAAACCG GACAGGCAAC TGTCCGGTTT TTTGTTGTCT
    GCAAAGGATT TCAGGCATCC

721 GGT.
```

The above opm25 amplification product encodes, from nucleotides 1-642, a deduced Omp25 protein:

```
                                  (SEQ ID NO: 10)
  1 MRTLKSLVIV SAALLPFSAT AFAADAIQEQ PPVPAPVEVA
    PQYSWAGGYT GLYLGYGWNK

 61 AKTSTVGSIK PDDWKAGAFA GWNFQQDQIV YGVEGDAGYS
    WAKKSKDGLE VKQGFEGSLR

121 ARVGYDLNPV MPYLTAGIAG SQIKLNNGLD DESKFRVGWT
    AGAGLEAKLT DNILGRVEYR

161 YTQYGNKNYD LAGTTVRNKL DTQDFRVGIG YKF.
```

The iaIB gene sequence amplified from *B. melitensis* 16M genomic DNA (excluding flanking restriction sites added by primers) was:

```
                                  (SEQ ID NO: 11)
  1 ATGAAAAATT ATCGTGCAAT CGGTCTTGCA TTCACGTTCA
    CTGCCCTTTC CAGTCTTTCG

 61 GCCTTTGCAG CCTCCCTGCC CGGCGGAGCA AGCACCTTGC
    AGGAAACCTA TCAGGACTGG

121 ACCGTGTCTT GCCAGTCGCA GAAGGATACA ACAGCCTGCG
    TGATGCGTCA GGAGCAAAGC

181 AGCGCCCAGG CCGGCCAGCG CGTTCTGACT GCCGAGCTGC
    GCAACGTCGC CGGCGGCAAA

241 GTTGACGGTG TGTTGCTGAT GCCGTTCGGT CTTGATCTTG
    CCAAGGGCGC CTCGCTCAAG

301 ATTGATGACA CCGCTGGGCC AAACCTCACC TTCTCCACCT
    GCCTGCCGCA GGGCTGCCTC

361 GCGCCAGTGA GCTTCGATGC CAAGCAGGTT GCTGCGCTGA
    AATCCGGCAC CAACATCAAT

421 GTCACCACGA CGGCGCTCAG CCCGAGCCAG CCGGTTGCCT
    TCAAGATTTC CCTGAAAGGC

481 TTCGGTGCCG CGCTCGACCG CATTCAGGCA TTGACCAAGT
    AA.
```

The above iaIB amplification product encodes, from nucleotides 1-522, a deduced IaIB protein:

```
                                  (SEQ ID NO: 12)
  1 MKNYRAIGLA FTFTALSSLS AFAASLPGGA STLQETYQDW
    TVSCQSQKDT TACVMRQEQS

 61 SAQAGQRVLT AELRNVAGGK VDGVLLMPFG LDLAKGASLK
    IDDTAGPNLT FSTCLPQGCL

121 APVSFDAKQV AALKSGTNIN VTTTALSPSQ PVAFKISLKG
    FGAALDRIQA LTK.
```

The iaIB gene of SEQ ID NO: 11 has been designated with the locus tag BMEI1584 on chromosome 1 of *Brucella melitensis* strain 16M (full chromosome sequence available as Genbank accession No. NC_003317, which is incorporated by reference in its entirety).

In Vitro Characterization of Candidate Vaccines

The identity of plasmid constructs produced as described above from the amplified omp25 and iaIB genes was confirmed through sequencing. Endotoxin content of preparations was determined to be less than 1.0 E.U. per ml. Specific antigen transcription was demonstrated from each of the DNA vaccine plasmids following transfection of Cos7 cells, total RNA harvest and candidate specific RT-PCR. Specific transcript was detectable in total RNA from 24 hours post-transfection. Transcript was also confirmed at 48 and 96 hours post-transfection (data not shown).

Immunogenicity of Novel DNA Vaccines: *Brucella* Specific Antibody Production

Of the candidates investigated in this experiment, the p-omp25 and p-iaIB vaccines produced a significant *Brucella* specific response with 100% of p-iaIB and 60% of p-omp25 inoculated mice generating positive IgG1 and, or, IgG2a responses. The data is summarized in Table 4.

TABLE 4

*Brucella* specific seroreactivity at two-weeks post vaccination (week 11).

| Vaccine group | IgM | IgG1 | IgG2a |
|---|---|---|---|
| Rev.1 (at 2 weeks post-vaccination) | 100% [0.603 ± 0.39] | 0% [0.08 ± 0.01] | 0% [0.08 ± 0.01] |
| Rev.1 (at 11 weeks post-vaccination) | 100% [0.746 ± 0.35] | 100% [1.649 ± 1.584] | 100% [2.800 ± 1.41] |
| PBS | 0% [0.105 ± 0.02] | 20% [0.065 ± 0.21] | 0% [0.079 ± 0.01] |
| pcDNA3.1 | 0% [0.073 ± 0.001] | 0% [0.065 ± 0.02] | 20% [0.081 ± 0.03] |
| p-omp25 | 20% [0.096 ± 0.19] | 20% [0.251 ± 0.49] | 60% [0.493 ± 0.48] |
| p-ialB | 80% [0.240 ± 0.12] | 80% [0.165 ± 0.08] | 100% [0.96 ± 1.14] |
| ASSAY C/O | 0.250 | 0.151 | 0.089 |

Data presented as % of animals determined as positive [Mean OD of group responses ± standard deviation].
Positive samples determined as individual OD above plate Cut-off (C/O) OD.
Plate CO determined as mean + 2X standard deviations Normal mouse (Sigma) negative control serum OD.

Immunogenicity of p-omp25, p-iaIB and p-fliC: *Brucella* Specific Recall Cytokine Responses

*Brucella* antigen specific cytokine production was measured following in vitro stimulation of splenocytes from vaccinated mice, harvested at three week intervals during the course of vaccinations and at 12 weeks after the completion of the vaccination protocol. These data are summarized in Table 5. These results indicated elevation of *Brucella* specific IFNγ and TNFα production in the p-omp25 and p-iaIB vaccine groups compared to vector (pcDNA3.1 inoculated) controls. IL-4 and IL-10 production were not observed.

TABLE 5

In vitro cytokine production from p-omp25 or p-iaIB vaccinated mice in response to stimulation with *Brucella* antigen stimulation.

| | Week 2 | Week 5 | Week 8 | Week 11 | Week 21 |
|---|---|---|---|---|---|
| | | | IFNγ | | |
| p-omp25 | − | +++ | + | + | + |
| p-ialB | − | − | − | + | + |
| | | | TNFα | | |
| p-omp25 | − | + | + | + | + |
| p-ialB | − | +++ | − | + | + |
| | | | IL-4 | | |
| p-omp25 | − | − | − | − | − |
| p-ialB | − | − | − | − | − |
| | | | IL-10 | | |
| p-omp25 | − | − | − | − | − |
| p-ialB | − | − | − | − | − |

Table indicating the response of vaccinated mice to *Brucella* antigen (whole *B. melitensis* 16M @ 40 μg/ml). To generate this summary: specific Net cytokine responses were determined as [concentration (pg/ml) cytokine in stimulated SN] − [concentration (pg/ml) cytokine in unstimulated SN].
Data was then adjusted to provide the mean concentration of net cytokine [pg/ml] observed in the SN of a group (n = 3) for the vaccine group minus the mean concentration of net cytokine [pg/ml] observed in the SN of the corresponding group (n = 3) of p-vector inoculated group. Where significant (Mann-Whitney test, p, 0.05) specific increases were observed between groups (specific vaccine compared against PBS vector control) the mean concentration of induced cytokine is depicted in the table in terms of + as follows: + 10–100 pg/ml, ++ 101–250 pg/ml, +++ 251–500 pg/ml. Negative (−) samples contain <10 pg/ml cytokine.

The Protective Efficacy of Vaccination in the BALB/c Mouse Against Challenge with *B. melitensis* 16M Standard challenge procedures revealed a statistically significant protective effect (one way ANOVA with Dunnetts post-test, comparing the *Brucella* load in the spleen of vaccinated and control (PBS inoculated) mice) in mice receiving vaccination with Rev.1 (3.63 PU), and also in mice inoculated with DNA constructs p-omp25 (2.54 PU) and p-iaIB (2.70 PU) ($p<0.05$). A significant protective effect was not observed from the pcDNA3.1 vector control inoculated groups ($p>0.05$). Evidence of a modest reduction of bacterial load was observed in the high dose challenge studies ($3.25\times10^5$ CFU per mouse) for the p-iaIB vaccinated group (0.93 PU) and p-omp25 vaccinated group (0.72 PU), but this was not revealed to be statistically significant. Notably, in these studies we were unable to confirm protective efficacy in any group, including the Rev.1 control group (0.36 PU). The protection data obtained are presented in Table 6.

TABLE 6

Protective efficacy of vaccination with DNA constructs in the BALB/c mouse.

| | Challenge A | | Challenge B | |
|---|---|---|---|---|
| Group | $Log_{10}$ CFU/ spleen | Protection units (PU) | $Log_{10}$ CFU/ spleen | Protection units (PU) |
| PBS | 4.72 ± 0.14 | 0 | 5.59 ± 0.36 | 0 |
| p-omp25 | 2.14 ± 1.3* | 2.54 | 4.88 ± 0.87 | 0.72 |
| p-ialB | 2.02 ± 0.54* | 2.70 | 4.66 ± 0.49 | 0.93 |
| pcDNA3.1 | 4.33 ± 0.64 | 0.39 | 4.9 ± 0.57 | 0.60 |
| Rev.1 | 1.10 ± 0.19* | 3.63 | 5.23 ± 0.45 | 0.36 |

Protection units calculated as [mean $Log_{10}$ CFU PBS − mean $Log_{10}$ CFU test group]
Rev.1 inocula [A] $1.14\times10^5$ CFU per mouse, [B] $0.97\times10^5$ CFU per mouse.
Challenge [A]: $0.87\times10^5$ CFU *B. melitensis* 16M/mouse. Challenge [B]: $3.25\times10^5$ CFU *B. melitensis* 16M/mouse.
*significant reduction in splenic load compared to PBS inoculated mice ($p\leq0.05$, One-way ANOVA with Dunnett's post-test).

Discussion

Example 1 shows the protective ability of p-omp25 and p-iaIB based vaccines.

RT-PCR was used to demonstrate transcription of each candidate gene from *Brucella* grown under standardized culture conditions, or *Brucella* infected spleen material. Verification of transcription was considered to be evidence of initiation of the expression process, and an indication that these genes were active in *Brucella*. The data indicated that iaIB and omp25 were transcribed under standard solid phase culture conditions and all other conditions investigated in this study, suggesting that expression of these genes is important enough to be conserved across these diverse conditions.

Serological recognition of candidate antigens by infected sheep was used as an additional tool to support candidate selection. The presence of specifically reactive antibodies was used to demonstrate that the proteins were immunogenic, and thus of possible significance to the outcome of infection. Candidates shown to be transcribed under all conditions assessed correlated with the proteins most frequently recognized by the humoral immune response of infected sheep, and more significantly were subsequently found to be the most successful candidates in terms of protective efficacy. Subsequent analyses of these same sera against a purified recombinant omp25-GST antigen and a purified recombinant iaIB antigen produced identical results to the crude lysates for these proteins in terms of the detection of positive responses from infected animals (data not shown), suggesting that these lysate ELISAs are an accurate reflection of specific seroreactivity at least in the case of these particular antigens. For the purposes of this study, the demonstration of serological responses from infected sheep was considered evidence of the natural immunogenicity of the candidate antigen.

Vaccine immunogenicity and protective effect was assessed in a mouse model. Immunogenicity was initially assessed in terms of *Brucella* reactive antibodies. A qualitative indication of immune response was obtained through assessment of specific isotypes of antibody. Protective efficacy was demonstrated in terms of the reduction of *Brucella* load in the spleens of vaccinated mice in comparison to naïve mice following challenge according to a standardized model. Specific antibody responses were recorded for p-omp25 and p-iaIB. Significantly, IgG2a responses were evident in p-omp25 and p-iaIB inoculated mice. These findings are significant in that clearance of *Brucella* infection is correlated with the generation of Th1 effectors: IFNγ, TNFα and IL-12 are all important cytokines. In these studies p-omp25 and p-iaIB were shown to have protective activity and induce detectable IgG2a.

A protective effect from p-omp25 and p-iaIB was determined in the $10^4$ CFU challenge study through comparison of the *Brucella* load in the spleens of vaccinated and unvaccinated (PBS inoculated) mice. We were unable to recover viable *Brucella* from the spleens of 60% (three out of five) of p-iaIB or p-omp25 treated mice of a study group following challenge with $\sim1\times10^4$ CFU *B. melitensis* 16M per mouse. The remaining two mice in these groups also showed significantly reduced *Brucella* loads compared to the unvaccinated (PBS and vector control) mice. If the data are considered in terms of the % of animals without detectable *Brucella* in their spleens (less than 10 CFU per spleen) at 15 days post-challenge, the effect of the p-iaIB and p-omp25 vaccinations is judged to be equivalent to that of the Rev.1 live attenuated vaccine, with each vaccine able to 'protect' 60% of the test population. Moreover, a comparison of the total quantitative data available from each sample shows the *Brucella* load of the p-omp25, p-iaIB and Rev.1 vaccinated animals to be significantly lower ($p<0.05$, One-Way ANOVA, Dunnett's post-test) than that observed for the unprotected controls (PBS or pcDNA3.1 vector control vaccinated mice). Each of these vaccines was shown to have a protective index of greater than 2.5.

The demonstration of protective efficacy from p-omp25 and p-iaIB vaccination prompted further investigation into these particular candidate vaccines. Further experiments were set up to include direct measurement of *Brucella* specific cell mediated immune effectors. For the p-omp25 vaccine evidence for *Brucella* specific recall IFNγ and TNFα was obtained after the second inoculation and maintained following the third and fourth inoculation. IL-4 or IL-10 were not detected. Moreover, *Brucella* specific IFNγ was still evident at 12 weeks post-vaccination, albeit at low concentration, indicating generation of a lasting Th1 immune response. For p-iaIB vaccination, IFNγ was detected but specific IFNγ was not detected until after the fourth vaccination. Notably, this low level IFNγ was also demonstrable at 12 weeks post-vaccination, indicating that although relatively weak the response was persistent.

The two protective vaccines identified in this study (p-omp25 and p-iaIB) effected a considerable reduction of splenic *Brucella* compared to the PBS unprotected control (2.45 or 2.7 protection units or ≥99% reduction of actual numbers). This represents an improvement over the protective efficacy so far described for other *Brucella* specific DNA vaccines

EXAMPLE 2

Use of Cationic Liposome Delivery to Improve DNA Vaccine Efficiency

We have previously shown (see Example 1) that two DNA vaccines based upon the *B. melitensis* 16M genes iaIB and omp25 were protective in the BALB/c mouse model of brucellosis. Protection was conferred using an initial vaccination of 100 μg naked plasmid DNA followed by three booster vaccinations of the same amount. The present example shows that liposome-bound formulation of the DNA elicited an improved response in the case of the IaIB antigen compared with a single dose of naked DNA vaccination. Example 2 in part includes data previously described for the p-omp25 vaccine (but not the p-iaIB vaccine) in Commander et al. (2004, Poster presentation at "DNA Vaccines 2004" Conference, Monte Carlo, Monaco, November 16-19).

Materials and Methods

Most materials and methods are as described in Example 1 above. For immunogenicity assessments, antibody production was measured by an alternative ELISA (16M antigen, recombinant Omp25-GST and recombinant IaIB) using purified antigen (see below).

IFN-γ ELISPOT assays were used to assess the antigen specific immune response of vaccinated mice both pre- and post-challenge (see below).

Collection and Processing of Serum Samples from Mice

Blood samples were collected from individual vaccinated and infected mice at various times for assessment of specific serological responses. Blood was collected following venous puncture of the tail. Each sample was incubated at RT for 2-4 hours and 4° C. overnight, before centrifugation at 3000 rpm (Hereaus Biofuge Fresco) for 30 minutes. The serum was transferred to a fresh labeled eppendorf tube and incubated at 56° C. for 30 minutes to inactivate complement. The total volume of serum collected from an individual mouse at any time during these studies ranged between 10 and 80 μl of serum. Samples were stored frozen at −20° C. until required. 10 μl of serum from each individual mouse in a group were combined to provide the pooled samples. Pooled samples were also stored at −20° C.

*B. melitensis* 16M Whole Antigen ELISA for Detection of *Brucella* Specific Antibodies in Mouse Sera 16M antigen was prepared from solid phase cultures grown on SDA+10% horse serum. Cultures were harvested after 4 days growth, and cells were washed twice by centrifugation (4000 rcf, for 10 minutes at 4° C.) and resuspended in a minimal volume of sterile water. The preparation was rendered non-viable through heating to 80° C. in a water bath for 90 minutes. The 16M antigen was then coated to Maxisorp™ 96 well plates (Nunc). Antigen was diluted to 50 μg/ml in Carbonate Coating Buffer (CCB): 0.034 mM Sodium hydrogen carbonate, 0.016 mM sodium carbonate, pH 11.0, and applied to plates at 50 μl per well. Plates were incubated at 4° C. overnight. Plates were washed twice with PBS-T wash buffer and 200 μl per well of blocking solution (4% skimmed milk powder (Marvel) in PBS-EDTA buffer) was added to the plates, which were incubated at RT for ~2 hours. Test sera and the selected control samples were prepared for analysis by dilution 1% marvel PBS-EDTA diluent buffer. Normal mouse sera (Sigma) was used as a negative control in these ELISAs. Positive control serum was obtained from mice that had been infected with *B. melitensis* 16M. The serum was collected from 10 *B. melitensis* 16M infected mice at day 84 post-infection and pooled for use as a positive control.

After blocking, plates were washed once in PBS-T wash buffer and the test serum dilutions and controls applied to the plate. Each individual dilution/sample was plated into sufficient wells (50 μl per well) to permit assay of relevant isotype specific responses in duplicate. Plates were incubated at 37° C. for 90±10 minutes. Plates were then washed five times with PBS-T. Isotype specific anti-mouse Ig enzyme conjugated reagents were used as detection antibodies. Rat anti-mouse IgM (p chain specific) peroxidase conjugated antibody at 1 in 2000 in diluent buffer, Goat anti-mouse IgG1 peroxidase conjugated antibody (STAR81 P, Serotec) at 1 in 1000 in diluent buffer, and Goat anti-mouse IgG2a peroxidase conjugated antibody (STAR82P, Serotec) at 1 in 1000 in diluent buffer were used. These antibody solutions were applied in 50 μl per well volumes and incubated at 37° C. for 1 hour. Plates were washed 5 times with PBS-T and blotted dry onto absorbent matting. TMB (3'3'5'5' Tetramethylbenzidine) working solution was prepared from the stabilized Substrate and Chromogen solutions (Vetoquinol) and added to the plates (100 μl per well). Plates were incubated for 10-30 minutes in the dark for reaction development. Reaction development was judged by eye, and when the IgG2a positive control wells had achieved sufficient intensity of color, the reaction was stopped by the addition of 100 μl per well of 0.1 M Citric acid solution. Plates were read within 1 hour of reaction completion using a Titertek Multiscan II to determine optical density at 450 nm.

OMP25-GST and GST ELISAs, for the Detection of OMP25 Specific Antibodies in Mouse Sera This procedure is essentially identical to that of the 16M antigen ELISA, except for the initial antigen coating stages. In this ELISA recombinant fusion protein Omp25-GST prepared from the pGEX-omp25 construct and purified under contract by Lionex GmbH, was used as the antigen. Antigen was prepared in Coating buffer to a concentration of 5 μg/ml (or 0.5 μg/well) and incubated at 4° C. overnight for the initial coating step. The rest of the procedure was performed identically to the 16M ELISA.

Recombinant IaIB ELISA for the Detection of IaIB Specific Antibodies in Mouse Sera This procedure is essentially identical to that of the 16M antigen ELISA, except for the initial antigen coating stages. In this ELISA recombinant fusion protein IaIB prepared from a pGEX-IaIB construct and purified under contract by Lionex GmBH was used as the antigen. Antigen was prepared in Coating buffer to a concentration of 15 μg/ml (or 1.5 μg/well) and incubated at 4° C. overnight for the initial coating step. The rest of the procedure was performed identically to the 16M ELISA.

Brucellergene™ ELISA for the Detection of *Brucella* Specific Antibodies in Sheep or Goat Sera An ELISA was developed to assess the reactivity of serum samples from *Brucella* infected sheep and goats against protein antigens of *Brucella*. Brucellergene™, which is free from the serodominant LPS of smooth *Brucella* spp., was used in these studies was coated to Maxisorp plates at a concentration of 45 μg/ml or 2.25 μg per well in CCB. Plates were incubated overnight at 4° C. The assay was essentially identical to that described for assessment of mice samples with whole *Brucella* 16M antigens, except that test serum was diluted 1 in 200 in diluent buffer for analysis, and identification of separate isotype antibody responses was not performed. An Anti-sheep IgG Horse Radish Peroxidase conjugate was used at a dilution of 1 in 4000 in diluent buffer.

OMP25-GST and GST ELISAs, for the Detection of OMP25 Specific Antibodies in Sheep or Goat Sera ELISA plates were coated as described for the analysis of mice samples. The assay was performed identically to that described for analysis of sheep and goat samples in the Brucellergene™ antigen ELISA.

Invasion Protein B Specific ELISA for the Detection of Invasion Protein B Specific Antibodies in Sheep or Goat Sera ELISA plates were coated as described for the analysis of mice samples. The assay was performed identically to that described for analysis of sheep and goat samples in the Brucellergene™ antigen ELISA.

Liposome Production and Complexing with DNA

Lipid vesicles were prepared from 1-monopalmitoyl glycerol, cholesterol stearyl amine and Cetyl Trimethyl Ammonium Bromide (CTAB) in the molar ratio 5:4:1:1, by the method described previously (Brewer et al., 1998, supra). Plasmids were surface-adsorbed to cationic lipid vesicles immediately prior to administration. Briefly, 2 ml plasmid DNA at 1 mg/ml was added dropwise to an equal volume of liposome preparation. Liposome:plasmid mixture was incubated for 30 minutes at RT using a Denley Rotary Cell Mixer, and then centrifuged at 2000 rcf (Hereaus Microfuge) to sediment the liposomes. 2 ml of SN was removed. Remaining plasmid:liposome suspension was mixed gently and used within 1 hour for the inoculation of mice. The 2 ml SN sample was retrospectively assessed for the presence of residual DNA by spectrophotometry and agarose gel electrophoresis.

Cell Mediated Immunology

In addition to the measurement of antibodies, the cell mediated immune responses of vaccinated and infected BALB/c mice were also investigated. For these assessments mouse splenocytes were isolated and fractionated. Cytokine production in response to *Brucella* specific in-vitro stimulation was measured using commercially available cytokine ELISAs from Biosource and in-house optimized ELISPOT procedures.

Spleen Harvest and Isolation of Splenocytes for CMI Investigations

Mice were sacrificed by cervical dislocation and spleens were aseptically removed. Spleens were placed immediately in pre-warmed (37° C.) DMEM complete media (DMEM+Non essential amino acids, 1,000 U/ml Penicillin, 100 μg/ml Streptomycin, 25 μg/ml Amphotericin B, and 10% Fetal Bovine serum), in order to preserve viability. Spleens were diced using sterile surgical scissors and macerated with the barrel of a 5 ml Syringe through a 80 μM mesh cell sieve to release splenocytes into the media. Splenocyte suspensions were washed twice in FACSflow Sheath Fluid Buffer [FF] by centrifugation at 330 rcf (Hereaus MegaFuge) for 15 minutes at 4° C., and resuspended in a minimal volume (~1 ml) of FF buffer Viable cells were enumerated after suspension of 50 μl of cell suspension in 450 μl of White cell counting fluid (1% glacial acetic acid in D-PBS, with a trace of Gentian Violet Dye), using the Neubauer Haemocytometer. Cells were reconstituted to $5\times10^6$/ml in DMEM complete for stimulation for ELISA or ELISPOT reactions or used in T cell subset depletion studies according to the protocol described below.

T Cell Sub-Set Depletion Procedures

MidiMACS™ (Miltenyi Biotech) technology was used for the depletion of T cell subsets from the whole splenocyte preparations. Anti-mouse CD4+ (L3T4) magnetic beads were used to bind CD4+ expressing cells, and Anti-mouse CD8+ (Ly-2) magnetic beads were used to bind CD8+ expressing cells from the total splenocyte population. Cell concentrations were adjusted to a total of $1\times10^9$/ml by dilution in FF buffer and 100 μl of bead suspension was added to each 1 ml of cell suspension. Magnetic beads and cells were incubated on ice for 30 minutes with occasional gentle mixing. MACS LS columns were equilibrated with 3 ml of ice cold FF Buffer, and positioned within the MidiMACS™ magnets. Bead treated cell suspensions were applied to the LS columns and the fall through fraction collected in a sterile Falcon Tube over ice. Columns were washed through with 3×3 ml of ice cold FF. Again the eluted fraction was collected. Total eluate was diluted in ice cold FF and washed by centrifugation (300 rcf, 15 minutes, 4° C., (Hereaus MegaFuge)), and resuspended in a minimal volume of ice cold FF. Cells were enumerated and diluted to a final concentration of $5\times10^6$/ml in DMEM Complete for use in stimulation assays.

Stimulation of Splenocytes with Specific Antigens

Antigens and control mitogen solutions were prepared to appropriate concentrations in DMEM Complete media. The lectin Concanavalin A Type IV purified (Con A) was used as the non-specific mitogen throughout the study; Con A was prepared in DMEM complete to a concentration of 10 μg/ml. Specific antigens were prepared to the following concentrations, Brucellergene™: 80 μg/ml, Recombinant OMP25-GST: 20 μg/ml, Recombinant GST: 20 μg/ml. Recombinant Invasion protein B: 30 μg/ml. Heat killed *Brucella melitensis* 16M antigen: 50 μg/ml. Antigen preparations were added to designated wells in either 96 well pre-coated IFN-γ ELISPOT plates (100 μl volumes per well), or sterile 24 well tissue culture plates (500 μl volumes per well). An equivalent volume of cells at a concentration $5\times10^6$/ml were added directly to the appropriate wells containing antigen. Thus, wells contained cells at a final concentration of $2.5\times10^6$/ml in either DMEM complete or a DMEM complete solution of 5 μg/ml Con A, 40 μg/ml Brucellergene™, 10 μg/ml OMP25-GST, 10 μg/ml GST or 15 μg/ml Invasion protein B. Stimulation cultures were incubated at 37° C., 5% $CO_2$ for either 24 (ELISPOT) or 48 (SN ELISA) hours.

IFN-γ ELISPOT

For ELISPOT assays 96-well PVDF membrane filter plates were pre-coated with 1.5 μg/ml well of Anti-Mouse IFN-γ monoclonal (AN18) 18 to 24 hours prior to harvest of splenocytes. On the day of splenocyte harvest plates were washed 2× with PBS and blocked with 200 μl per well with DMEM Complete medium for 2-4 hours at 37° C. prior to addition of cells. Splenocytes were harvested and stimulated as described above. The ELISPOT plates/stimulation cultures were incubated for 24±2 hours, loosely wrapped in aluminum foil, at 37° C. in a 5% $CO_2$ atmosphere incubator. Following incubation cells were aspirated from the filter plates using a multichannel pipette, and taking care not to damage the membrane. Plates were washed 4× with PBS-T wash buffer, and blotted dry after the final wash. Anti-Mouse IFN-γ biotinylated antibody was prepared to a concentration of 1 μg/ml in ELISPOT diluent Buffer (1% BSA in PBS), and 100 μl per well was applied to the plates. Plates were incubated at 25° C. for 1 hour wrapped loosely in aluminum foil. Following incubation plates were washed 4× with PBS-T wash buffer, and blotted dry after the final wash. Streptavidin Alkaline Phosphatase reagent was diluted 1:1000 in ELISPOT diluent buffer and 100 μl per well added to the plates. This stage was incubated at 25° C., plates wrapped loosely in foil, for 1 hour. After incubation plates were washed 4× with PBS-T wash buffer and 2× with distilled water, and blotted dry onto absorbent toweling. BCIP-NBT fast Tabs™ were used to prepare the substrate solution. 1 tablet was dissolved in 10 ml of pre-warmed distilled water, and filtered through a 0.2 μM syringe filter prior to use. Substrate solution was applied to wells at 100 μl per well, and plates were incubated in the dark at 25° C. for between 10 to 30 minutes. Reactions were halted once the color development in the Con A stimulated sample wells was considered to be complete. Rinsing the plates at least twice in distilled water stopped reactions. The under drain section of the plate was then removed and the plates incubated at 37° C. overnight in order to dry the filters.

Since these assays involved splenocytes isolated from 16M or Rev.1 infected mice, the splenocyte cultures were potentially infected with live *Brucella* spp., and procedures had to be conducted in a containment level III facility. Plates were fumigated (using standard formaldehyde fumigation procedures validated for use against *Brucella* spp.), before being removed from the facility for reading. Plates were read using an AID ELISPOT plate reader.

Measurement of SN Cytokine Concentration by ELISA

For ELISA work, stimulations were performed as described above using 1 ml total volumes per reaction (500 μl of antigen preparation and 500 μl of cells) in 24-well plates. Plates were wrapped loosely in foil and incubated at 37° C., 5% $CO_2$. After 72 hours incubation, the plates were centrifuged to sediment cells and the SN dispensed in 200 μl aliquots into sterile 96 well plates. These samples were treated with Sodium azide in order to kill *Brucella* and frozen at −80° C. until required for use in ELISA. Commercially available cytokine detection ELISA reagents were used to measure the presence of the cytokines IL-4, TNF-α, IL-12 and IFN-α in the SNs harvested from stimulated splenocytes. ELISAs were conducted according to manufacturer's recommendations.

Samples were defrosted and applied to appropriate wells of the test plate. Recombinant mouse cytokines supplied with the kits were prepared in diluent buffer to generate a standard curve for quantitative analysis of the results. A series of these 'standards' were included in each assay. Cytokine concentration [pg/ml] in SNs was calculated through linear regression using GraphPad™ Prizm software, to generate a curve of the known concentrations [pg/ml] plotted against the O.D. values of the standards. The concentration of cytokine in each unknown sample was interpolated from its O.D. value. Where sample O.D.s were found to be out of range for the standard curve the sample was retested following dilution in the appropriate standard diluent buffer.

For IFN-α and TNF-α analysis the SN from individual mouse splenocyte cultures were analyzed in ELISA. Each sample was tested in duplicate. For other cytokines, SN was pooled for analysis, such that each sample consisted of the combined SN of three mice from a single vaccine group stimulated with a single antigen. Pooled samples were also tested in duplicate in the ELISAs.

Experimental Strategy

The protective efficacy and immunogenicity of naked DNA and liposome formulated DNA vaccination was assessed. As this investigation required the comparison of protective efficacy and immunogenicity of a considerable number of groups of mice, it was not possible to conduct all experiments concurrently. Thus, the data presented herein are the result of three separate in-vivo investigations. The BALB/c mouse brucellosis model was used in all studies, and appropriate control groups of unvaccinated mice, pcDNA3.1 inoculated mice and Rev.1 vaccinated mice were included in each experiment. These studies can be summarized as follows:

1. p-omp25 [X1] vs p-iaIB [X1]: A comparison of the protective efficacy of single dose naked DNA vaccination with either p-omp25 or p-iaIB.
2. L-p-omp25 [X1] vs p-omp25 [X4]: A comparison of the protective efficacy of a single dose of liposome adsorbed p-omp25 (L-p-omp25 [X1]) with multiple dose naked p-omp25 (p-omp25 [X4]) vaccination.
3. L-p-iaIB vs p-iaIB [X4]: A comparison of the protective efficacy of a single dose of liposome adsorbed p-iaIB (L-p-iaIB [X1]) with multiple dose naked p-iaIB (p-iaIB [X4]) vaccination.

Results

The Production of Liposome Based Vaccines

DNA binding efficiency of the liposome preparations was assessed. Following mixing of the DNA and cationic liposome preparations, 50 μl of SN was removed from the mixture and analyzed by agarose gel electrophoresis and spectrophotometry. Neither method revealed the presence of plasmid DNA in the SN indicating that binding to the liposomes had been effective.

The Immunogenicity of the Vaccine Preparations

The capacity of vaccines to prime *Brucella* specific immune responses was measured in terms of specific antibody titer and the frequency and phenotype of antigen specific IFN-γ secreting cells detectable prior to challenge.

Specific Antibody Production

The antibody titer following vaccination was measured from each group of mice at two weeks post-vaccination. Single dose naked DNA and liposome vaccination titers were compared with data obtained from previous assessment of multiple dose naked DNA vaccinations. The data are summarized in Table 7.

TABLE 7

A comparison of antibody responses following a single immunization with either naked DNA or liposome adsorbed DNA.

| ELISA | Titre of specific IgG1 and IgG2a antibodies in ELISA | | | | | |
|---|---|---|---|---|---|---|
| | Omp25-GST | | IalB | | 16M | |
| Isotype | IgG1 | IgG2a | IgG1 | IgG2a | IgG1 | IgG2a |
| p-omp25 [x1] | — | 1/320 | ND | ND | — | — |
| p-omp25 [X4] | 1/640 | 1/1280 | ND | ND | 1/420 | 1/520 |
| L-p-omp25 [X1] | 1/320 | 1/1000 | ND | ND | 1/640 | 1/1280 |
| p-ialB [X1] | ND | ND | — | — | — | — |
| p-ialB [X4] | ND | ND | 1/5210 | 1/5210 | 1/5210 | 1/5210 |

TABLE 7-continued

A comparison of antibody responses following a single immunization with either naked DNA or liposome adsorbed DNA.

| ELISA | Titre of specific IgG1 and IgG2a antibodies in ELISA | | | | | |
|---|---|---|---|---|---|---|
| | Omp25-GST | | IalB | | 16M | |
| Isotype | IgG1 | IgG2a | IgG1 | IgG2a | IgG1 | IgG2a |
| L-p-ialB [X1] | ND | ND | 1/270 | (1/30) | 1/500 | 1/120 |
| pcDNA3.1 [X1] | — | — | — | — | — | — |
| pcDNA3.1 [X4] | — | — | — | — | — | — |
| L-pcDNA3.1 | — | — | — | — | — | — |
| Liposome only | — | — | — | — | — | — |
| Rev.1 @ 2 weeks post-vaccination | — | — | — | — | — | — |
| Rev.1 @ 11 weeks post-vaccination | 1/640 | 1/640 | — | — | 1/2560 | 1/2560 |

ND: Not tested.

—: Negative sample (OD below assay cut off)

Data in Table 7 show that a single intramuscular inoculation of naked p-iaIB plasmid was not sufficient to generate a detectable level of specific antibodies in either the IaIB recombinant antigen ELISA or the 16M antigen ELISA Whereas, multiple inoculations of naked p-iaIB elicited strong and equal magnitude antibody titers of both IgG1 and IgG2a isotype. However, a single inoculation with 100 μg of p-iaIB surface adsorbed to cationic liposomes (L-p-iaIB) was able to generate detectable specific IgG1 and low titer IgG2a. The titer from L-p-iaIB group mice was low, and IgG1 isotype antibodies were the dominant class of antibody whereas high titer balanced IgG1 and IgG2a responses were detected following p-iaIB [X4]. Overall, the use of liposome delivery for the p-iaIB plasmid resulted in detectable antibody responses after a single inoculation, which was not demonstrable from mice inoculated with an equivalent quantity of naked DNA.

IgG1 and IgG2a Omp25 specific antibodies were detected following multiple inoculations with p-omp25 vaccine (p-omp25 [X4]). IgG2a titers were in excess of IgG1 titers. Omp25 specific IgG2a was recorded after a single inoculation (p-omp25 [X1]). Specific antibody was also detected in the serum of mice receiving liposome formulated L-p-omp25. A higher titer IgG2a response was observed from L-p-omp25 [X1] vaccinated mice than naked p-omp25 [X1] vaccinated mice. Furthermore, a detectable IgG1 response is achieved after a single inoculation with L-p-omp25 [X1] but not p-omp25 [X1]. The antibody response measured from L-p-omp25 [X1]p-omp25 [X1] and p-omp25 [X4] was dominantly IgG2a isotype.

IFN-γ Production from Vaccinated Mice Prior to Challenge

The results of the ELISPOT investigations to determine the frequency and phenotype of primed antigen specific IFN-γ effector cells are summarized in Table 8.

TABLE 8

A comparison of the frequency and phenotype of IFN-γ secreting cells from mice receiving various doses and formulations of DNA vaccines. Δ IFN-γ secreting cells per million in response to stimulation with specific antigens.

| Vaccine | Net responsive cells: Total cell population | CD4+ depleted cell population | CD8+ depleted cell population |
|---|---|---|---|
| **Stimulation with recombinant Omp25-GST [10 μg/ml]** | | | |
| Liposome [X1] | 12.0 ± 2.21 | 0 | 0 |
| pcDNA3.1 [X1] | 0 | 0 | 0 |
| pcDNA3.1 [X4] | 0 | 0 | 0 |
| L-pcDNA3.1 [X1] | 0 | 0 | 0 |
| p-omp25 [X1] | 50.8 ± 24.9* | 27.8 ± 2.3 {↓45%} | 11.3 ± 2.3{↓78%} |
| p-omp25 [X4] | 73.3 ± 20.3* | 41.0 ± 5.2 {↓44%} | 10.8 ± 3.5 {↓85%} |
| L-p-omp25 [X1] | 25.0 ± 0.77* | 2.8 ± 0.08 {↓89%} | 13.0 ± 0.9 {↓48%} |
| **Stimulation with recombinant IalB [20 μg/ml]** | | | |
| Liposome [X1] | 10.25 ± 1.75 | 0 | 2.25 ± 1.77 |
| pcDNA3.1 [X1] | 17.25 ± 2.00 | 32.0 ± 17.58 | 11.25 ± 5.57 |
| pcDNA3.1 [X4] | 0 | 0 | 0 |
| L-pcDNA3.1 [X1] | 28.75 ± 19.12 | 7.05 ± 4.05 | 0 |
| p-ialB [X1] | 12.75 ± 1.75 | 0 | 0 |
| p-ialB [X4] | 75.02 ± 18.37* | 11.0 ± 4.85 {↓85%} | 36.25 ± 2.92 {↓52%} |
| L-p-ialB [X1] | 23.25 ± 6.06 | 0 | 0 |

The number of IFN-γ secreting antigen specific cells detected in splenocyte preparations from vaccinated mice. Data is displayed as Δ SFC/million, where Δ SFC is derived by subtraction of the background response of corresponding unstimulated cells. Data is displayed as mean Δ SFC/million ± Standard deviation.

*indicates SFC values significantly different to the vector and liposome control groups (ANOVA and Bonferroni's multiple comparison test, $p > 0.05$).

{↓ percentage decrease or inhibition of responder cell frequency from total cells}

The effector response of Rev.1 vaccinated mice was also measured in these investigations. Results showed that IFN-γ is mainly produced by CD4+ cells following vaccination with Rev.1.

The mean frequency of antigen specific IFN-γ secreting cells in the splenocyte populations of p-omp25 [X1] inoculated mice was modestly reduced in comparison to that observed under identical stimulation conditions for the p-omp25 [X1] vaccine: p-omp25 [X1] mean 50 SFC per million compared with p-omp25 [X4] mean 73 SFC per million. A direct statistical comparison of the number of SFC per well for the four replicate wells of each group sample showed no significant difference between the data sets (Mann-Whitney U test, p>0.05), suggesting an equivalent effect for the two vaccine strategies. IFN-γ production from both p-omp25 [X1] and p-omp25 [X4] mice was dominated by CD8+ T cells. This indicates that for this particular construct booster vaccinations do not significantly increase the frequency of antigen specific effector cells or alter the bias in CD4+: CD8+ priming.

For the L-p-omp25 [X1] vaccinated mice, IFN-γ effector cells were detected at a lower frequency than the p-omp25 [X1] vaccinated mice but this difference was not determined to be statistically significant (Mann-Whitney U test, p>0.05). However, a statistically significant difference in the SFC from p-omp25 [X4] and L-p-omp25 [X1] vaccinated mice was observed (Mann-Whitney U Test, p=0.0286). T cell subset depletion assays revealed that the majority of IFN-γ secreting cells in the splenocyte population from L-p-omp25 [X1] samples were CD4+ cells. This is in direct contrast to the data from the samples obtained from mice inoculated with naked p-omp25 where both single and four dose vaccination protocols elicited cells largely of the CD8+ phenotype.

For p-ialB vaccination the benefit of booster inoculations was more apparent. The p-ialB [X1] was unable to elicit statistically significant numbers of IalB specific SFC when compared to the SFC observed from pcDNA3.1 [X1] inoculation (Mann-Whitney U test, p>0.05). However, p-ialB [X4] group produced approximately 75 SFC per million, and Mann-Whitney U test revealed that this response was significantly different to that observed in both the pcDNA3.1 and p-ialB [X1] groups (p=0.0286).

The dominant phenotype of responder cells in p-ialB [X4] samples was shown to be CD4+ cells. L-p-ialB vaccination resulted in a low and statistically insignificant total number of SFC, when compared to the response observed from the control L-pcDNA3.1 group (p>0.05), and a lower mean total SFC than observed for p-ialB [X1]. Both CD4+ and CD8+ subset depletion eliminated the detectable response from the p-ialB [X1] or L-p-ialB samples.

The Protective Efficacy of the Various Vaccination Protocols

Due to the considerable numbers of mice involved in this investigation, it was not possible to conduct a single efficacy trial to compare all the selected vaccination strategies. Therefore, the protective efficacy of single dose naked DNA vaccination, multiple dose naked DNA vaccination, or single dose liposome formulated DNA vaccination was assessed in a number of separate experiments, as described above.

The assessments of protective efficacy of liposome formulations of L-p-omp25 [X1] and L-p-ialB (Experiments 2 and 3) were actually conducted concurrently, whereas a direct comparison of the protective efficacy of a single dose of the naked DNA vaccinations (p-ialB and p-omp25) was conducted in a separate study (Experiment 1). The data for protective efficacy are summarized in Table 9.

TABLE 9

The protective effect of vaccination with naked DNA or liposome formulated DNA.

| Vaccine group | *Brucella* CFU per spleen | *Brucella* per spleen as a % of challenge dose | Protection units |
|---|---|---|---|
| Experiment 1: A comparison of single dose naked DNA vaccine efficacy | | | |
| Rev.1 (V4) | 2.95 ± 0.35* | 67.8 | 2.04* |
| PBS | 5.00 ± 0.05 | 114.8 | 0 |
| pcDNA3.1 [X1] | 4.56 ± 0.31 | 104.8 | 0.43 |
| p-omp25 [X1] | 4.45 ± 0.44* | 102.3 | 0.55* |
| p-ialB [X1] | 4.19 ± 0.42* | 96.4 | 0.80* |
| Experiment 2: p-omp25 [X4] compared with L-p-omp25 [X1] | | | |
| Rev.1 (V1) | 4.28 ± 0.21 | 96.8 | 0.55 |
| Rev.1 (V4) | 1.47 ± 0.82* | 33.2 | 3.35* |
| PBS | 4.83 ± 0.29 | 109.2 | 0 |
| PcDNA3.1 [X4] | 4.80 ± 0.21 | 108.5 | 0.02 |
| p-omp25 [X4] | 1.40 ± 0.69* | 31.7 | 3.42* |
| L-p-omp25 [X1] | 4.01 ± 0.14* | 90.8 | 0.81 |
| L-pcDNA3.1 | 4.86 ± 0.44 | 109.8 | −0.03 |
| Experiment 3: p-ialB [X4] compared with L-p-ialB | | | |
| Rev.1 (V1) | 2.2 ± 1.0* | 51.2 | 1.83* |
| Rev.1 (V4) | 1.94 ± 0.77* | 44.8 | 2.12* |
| PBS [X4] | 4.10 ± 0.68 | 93.6 | 0 |
| PcDNA3.1 [X4] | 3.75 ± 0.36 | 86.1 | 0.32 |
| p-ialB [X4] | 1.91 ± 0.93* | 44.0 | 2.15* |
| L-p-ialB [X1] | 3.07 ± 1.08 | 70.5 | 1.00 |
| L-pcDNA3.1 | 3.37 ± 0.58 | 77.5 | 0.70 |

*Brucella* CFU per spleen: Log *Brucella* CFU per spleen ± standard deviation.

Protection units = Log *Brucella* CFU per spleen of unvaccinated mice − Log *Brucella* CFU per spleen of vaccinated mice. % Challenge dose: (Log CFU *Brucella* per spleen/Log CFU challenge dose) × 100.

*indicates statistically significant reduction of *Brucella* CFU per spleen compared to PBS controls (Mann Whitney U test, p < 0.05).

The data obtained in these investigations confirm a protective effect for Rev.1 (V4) vaccination in each experiment, and a protective effect from the four dose vaccination protocols for p-omp25 or p-ialB (p<0.05). Statistically significant reduction of bacterial load is also observed for p-omp25 [X1] and p-ialB [X1] vaccination (p<0.05), in Experiment 1. However, in terms of protection units this effect is slight and does not compare favorably with the protective effect of the multiple dose vaccines or the Rev.1 controls. Furthermore, these reductions are not significantly different (p>0.05) when compared to that observed in the pcDNA3.1 vaccinated mice.

In experiment 2, L-p-omp25 [X1] vaccination provided a 0.88 protection unit effect. Although a reduction in splenic *Brucella* was apparent this was not found to be statistically significant (p>0.05) in comparison to the unprotected controls.

L-p-ialB vaccination provided 1.0 unit of protection in Experiment 3, although this effect was not significant compared to the PBS, L-p-ialB [X1] or vector (pcDNA3.1) controls.

The Relationship Between Protective Efficacy and Vaccine Primed Antigen Specific Immune Responses To permit comparison of protective efficacy between experiments the *Brucella* load post-challenge for each vaccine group was presented as the percentage of the challenge dose. The mean log *Brucella* per spleen was calculated from the combined data from all three experiments. These values for protective effect were directly compared against the vaccine specific immune effectors measured during the investigations. These comparisons of protection against humoral immune responses and protection against IFN-γ secreting cells are presented in FIGS. 1 and 2.

FIG. 1 is a graphical representation of the data from protection trials and analysis of IFN-γ producing antigen specific cells detected in mice two weeks prior to challenge. Bacterial load represented as a percentage of the challenge dose in each study. Groups marked with * were shown to have a statistically significant protective effect. CD4+ cells=[Total SFC−CD4+ depleted SFC], CD8+ cells=[Total SFC−CD8+ depleted SFC].

Figure 2:
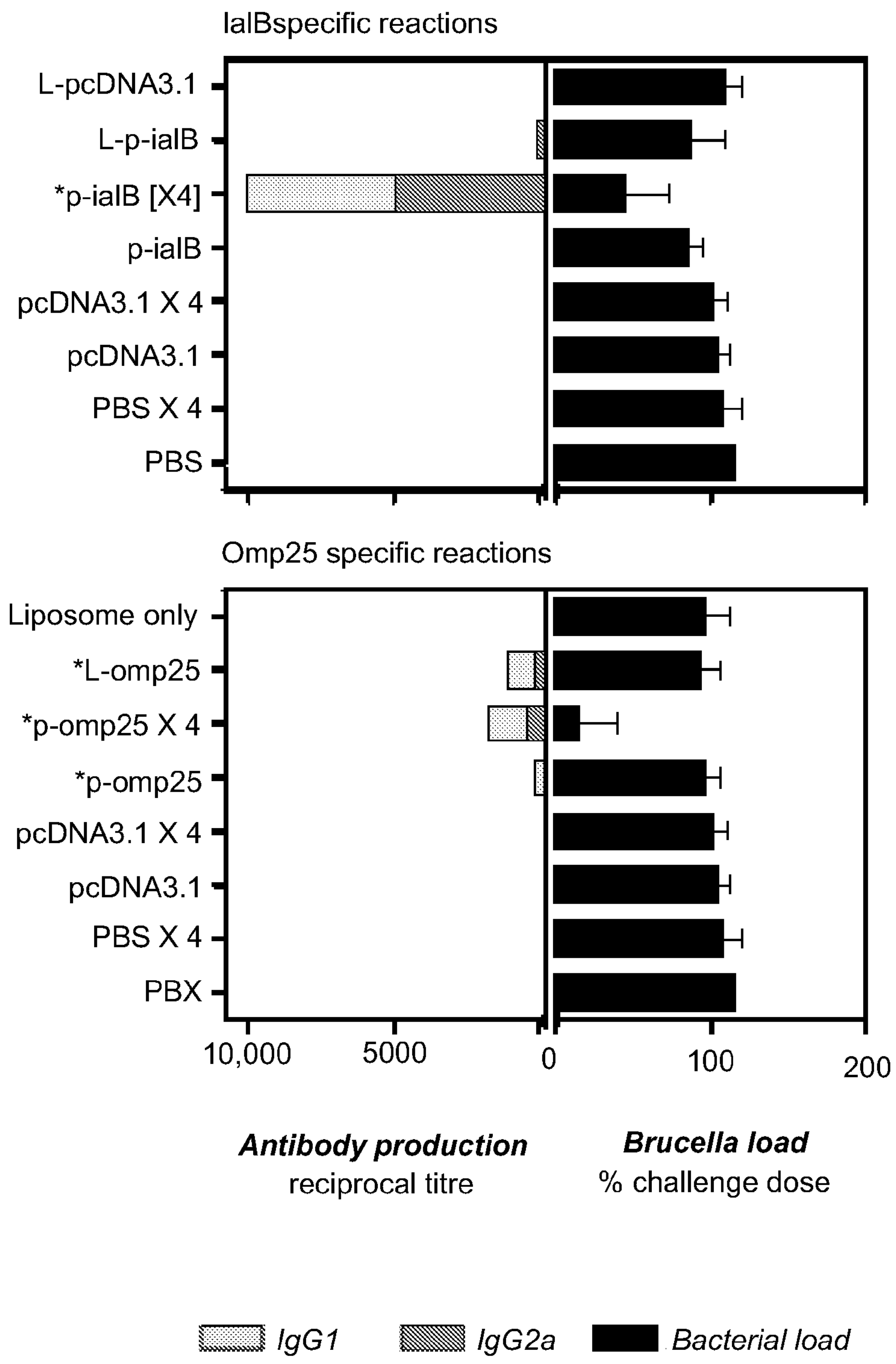
FIG. 2 is a graphical representation of the relationship between the protective efficacy of vaccination and the generation of specific antibodies.

FIG. 2 is a graphical representation of the data from protection trials and analysis of IFN-γ producing antigen specific cells detected in mice two weeks prior to challenge. Bacterial load represented as a percentage of the challenge dose in each study. Groups marked with * were shown to have a statistically significant protective effect. IgG1 and IgG2a titers measured.

FIGS. 1 and 2 show the immune responses alongside the observed protective effect of vaccination. The data show that antigen specific immune effectors, either IFN-γ secreting effector cells or specific antibody, are present in the protected animals prior to challenge.

Immune responses specific to the IaIB antigen are characterized by strong antibody responses and the priming of IFN-γ secretion from CD4+ T cells. A direct comparison of the total number of IaIB specific effector cells and protective effect of vaccination revealed a statistically significant correlation (Pearson correlation method, p=0.0066 (two-tailed), 95% confidence limits, $r^2$=0.7344), showing a direct relationship between the number of IaIB primed effector cells and the reduction of *Brucella* load in that group of mice. Antibody responses were also directly correlated with protective effect: Pearson analysis to compare antibody titer against protective effect revealed p=0.0024, $r^2$=0.8076, and p=0.0035, $r^2$=0.7836, for IgG1 and IgG2a respectively.

Omp25 specific responses were characterized by the priming of both CD8+ and CD4+ T cell responses, and production of relatively low titer antibody responses. Each of the omp25 based DNA vaccine formulations assessed were shown to have some level of protective activity in this model. A direct comparison of the total number of Omp25 specific cells and protective effect of vaccination revealed a statistically significant correlation (Pearson correlation method, p=0.0087 (two-tailed), 95% confidence limits, $r^2$=0.7095), showing a direct relationship between the number of Omp25 primed effector cells and the reduction of *Brucella* load in that group of mice. This relationship was preserved when the CD4+ depleted cell population response (i.e., the relative number of CD8+ T cells) was directly compared against the protective effect: p=0.0099, $r^2$=0.6793, but not when CD8+ depleted cell population (i.e. the relative number of CD4+ T cells) was compared against the protective effect (p>0.05). Antibody responses were also directly correlated with protective effect: Pearson analysis to compare antibody titer against protective effect revealed p=0.0015, $r^2$=0.8345, and p=0.0139, $r^2$=0.6631, for IgG1 and IgG2a respectively.

IFN-γ Production from Vaccinated Mice Post-Challenge

IFN-γ ELISPOT was conducted on splenocyte samples harvested during each of the protective efficacy bacterial enumeration studies. The aim of this investigation was to determine whether prior exposure to the candidate antigens resulted in measurably different responses to *Brucella* challenge. The results are summarized in Table 10.

TABLE 10

A comparison of the frequency of IFN-γ secreting cells from vaccinated mice that had been challenged with ~1 × $10^4$ CFU *B. melitensis* 16M. Δ IFN-γ secreting cells per million in response to stimulation with specific antigens.

| Vaccine group | Omp25 stimulation | IalB stimulation |
|---|---|---|
| Rev.1 | 60.00 ± 10.68 | 9.50 ± 11.50 |
| PBS | 146.75 ± 18.23 | 5.25 ± 2.73 |
| Liposome [X1] | 27.25 ± 8.99 | 1.00 ± 3.00 |
| pcDNA3.1 [X1] | 89.00 ± 6.69 | 0 |
| pcDNA3.1 [X4] | >500 | 0 |
| L-pcDNA3.1 [X1] | >500 | 0 |
| p-omp25 [X1] | 3.75 ± 1.77* | ND |
| p-omp25 [X4] | >500 | ND |
| L-p-omp25 [X1] | 46.25 ± 12.87 | ND |
| p-ialB [X1] | ND | 6.00 ± 0.62 |
| p-ialB [X4] | ND | >500 |
| L-p-ialB [X1] | ND | 43.50 ± 3.97 |

The number of IFN-γ secreting antigen specific cells detected in splenocyte preparations from vaccinated mice. Data are displayed as Δ SFC/million, where Δ SFC is derived by subtraction of the background response of corresponding unstimulated cells. Data are displayed as mean Δ SFC/million ± Standard deviation.
ND: Not determined.
>500 indicates saturated color development in the wells.
*sub-optimal assay: <200 SFC recorded following ConA stimulation for this group.

Table 10 shows the results of IFN-γ ELISPOT assays performed post-challenge. Splenocytes used in this assay were harvested and stimulated concurrently to the assays for enumeration of bacterial load. These data were directly compared against the protection data. This comparison in depicted in FIG. 3, which is a graphical representation of the data from protection trials and analysis of specific antibody production detected in mice two weeks prior to challenge. Bars represent mean values and error bars on protection data reflect standard deviation. Groups marked with * were shown to have a statistically significant protective effect. ^ indicates assay with sub-optimal positive control (ConA) responses.

Figure 3:
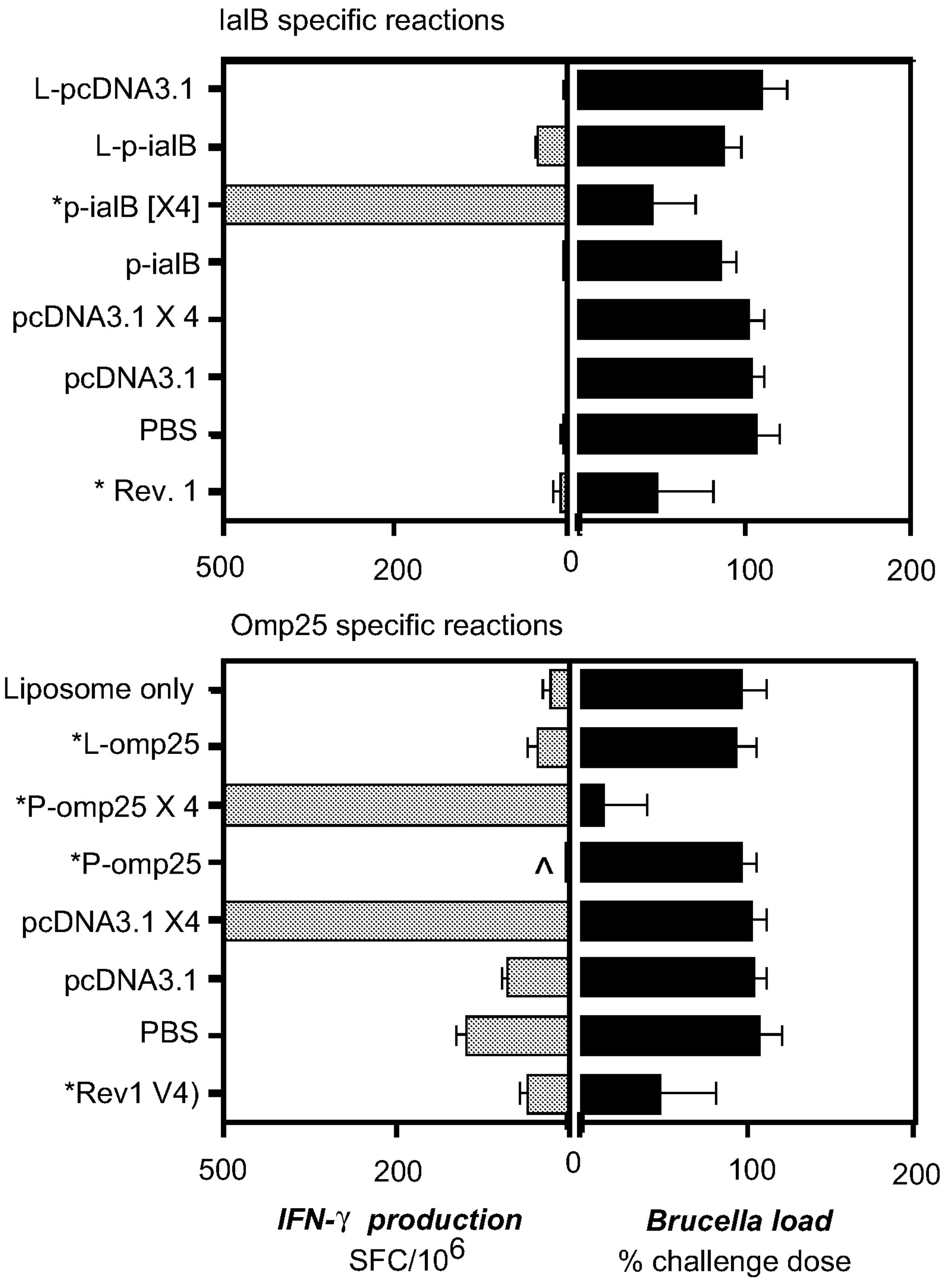
FIG. 3 is a graphical representation of the relationship between the protective efficacy of vaccination and the number of antigen specific effector cells detected post-challenge.

FIG. 3 shows the mean total IFN-γ secreting cells for each group compared to the bacterial load recovered from challenged mice. Omp25-GST reactive cells are detected regardless of vaccination status, and there is not a significant correlation between prior exposure to the Omp25 antigen and the production of Omp25 specific effector cells post-challenge. A Pearson correlation analysis of total effector cells compared to protective effect (in terms of % challenge dose) confirmed the absence of a measurable correlation (p=0.1136, $r^2$=0.3620). The result for p-omp25 [X1] is possibly not reflective of the actual Omp25 responsive cells in this sample: the mitogen control stimulation for this group also failed to reveal expected numbers of SFC, suggesting poor viability of this splenocyte preparation. However, even if these data are removed from the correlation analysis, a significant relationship between the number of IFN-γ secreting cells detected post-challenge and the protective effect cannot be measured.

Considerable numbers of IaIB specific effector cells were only detected in groups that had previously been exposed to the IaIB antigen, i.e. p-iaIB [X4] and L-p-iaIB [X1]. Very few IaIB primed IFN-γ secreting cells were detected in the Rev.1, PBS, and pcDNA3.1 groups. However, a significant correlation could not be demonstrated between the total number of IaIB specific effector cells and protection (Pearson correlation analysis, p=0.0785, r2=0.4277).

Discussion

An aim of this example was to re-evaluate the immunogenicity and protective efficacy of the p-iaIB and p-omp25 DNA vaccines, when administered as a single 100 μg intramuscular inoculation, and to compare these vaccines with vaccines surface absorbed onto cationic liposomes.

For both the p-omp25 and p-iaIB vaccines a multiple booster protocol consisting of four 100 μg doses of plasmid at three week intervals was the most successful approach in terms of protective efficacy. A slight protective effect was observed for the p-omp25 vaccine in a single dose protocol when the plasmid was delivered as either naked DNA (p-omp25 [X1]) or liposome adsorbed (L-p-omp25). A very slight protective effect was also observed for the p-iaIB [X1] vaccination, but protection was not indicated for the L-p-iaIB vaccination. Overall, the data showed that single doses of vaccine given either as naked DNA or as liposome adsorbed DNA was unable to provide equivalent protective efficacy to that observed following multiple inoculations. ELISPOT and ELISA techniques were used to analyze the capacity of the different vaccination strategies to prime IFN-γ secreting T cells and antibody production respectively, in the hope of explaining the qualitative differences in protection.

p-omp25 Specific Immunity

Single Versus Multiple Dose Naked DNA Vaccination

Antibody responses were demonstrable following a single 100 μg dose of naked p-omp25 vaccine. Further booster inoculations served to increase the titer of the specific response. Antibody responses were persistently dominated by high titer IgG2a, suggesting a strong Th 1 bias to the immune response. However, analysis of cellular effectors indicated that multiple booster vaccinations with naked p-omp25 (p-omp25 [X4]) did not result in significantly more antigen specific effector cells compared to the response elicited following a single vaccination (p-omp25 [X1]) (Mann Whitney U test $p>0.05$). This suggested that the increased protective effect of the multiple dose strategy is not achieved through generation of a greater magnitude of cellular response. Furthermore, both the multiple and single dose formulations of vaccine resulted in predominantly CD8+ IFN-γ responses. Depletion of the CD8+ subset resulted in a 77% and 85% reduction in the detected effector response for p-omp25 [X1] and p-omp25 [X4] respectively, suggesting a modest but statistically insignificant increase in the priming of CD8+ cells from the protective four dose p-omp25 [X4] protocol. Similarly, depletion of CD4+ cells resulted in a 44% decrease in the total number of cells for the p-omp25 [X4] vaccination, and a 45% decrease for the p-omp25 [X1], implying no difference in the ability of the two vaccines to prime CD4+ T cells. Since statistically significant differences in responses are not seen between p-omp25 [X1] and p-omp25 [X4] it is not possible to determine which subset of cells has the greatest impact upon the protective effect. Since it is known that the effectiveness of CD8+ T cells may be restricted to the early stages of brucellosis it is possible that the improved CD4+ response observed following repeated boosters is critical for the long term control of brucellosis.

Liposome Versus Naked DNA Vaccination

Liposome adsorption of the p-omp25 vaccine notably increased the antibody titer observed after a single inoculation, suggesting a considerable immunopotentiating effect from the liposome delivery. Notably, liposome delivery did not alter the bias of the IgG2a dominated response to this antigen. In contrast, the frequency of Omp25 specific IFN-γ secreting cells was not improved by liposome delivery of the vaccines, but differences in responsive T cell subsets were recorded. Non specific IFN-γ secreting cells were detected by ELISPOT from mice that had received inoculation with uncomplexed (without DNA) liposomes, suggesting an enhancement of non-specific IFN-γ production presumably triggered by activation of macrophages upon phagocytosis of the liposome particles. In this way the liposomes are anticipated to act as adjuvants as well as delivery vehicles for the DNA. However, this non-specific effect was not reflected in an increase of IFN-γ secreting cells for the L-p-omp25 [X1] vaccinated mice compared to the equivalent quantity of DNA delivered as naked DNA (p-omp25 [X1]): comparable frequencies of total antigen specific effector cells were detected from p-omp25 [X1] or L-p-omp25 [X1] groups.

Although similar frequencies of total effector cells were recorded in both groups, there were significant differences in the T cell subsets responding to p-omp25 [X1] and L-p-omp25 [X1] vaccination. Whereas CD8+ cells were the dominant type recorded from the splenocytes of p-omp25 [X1] vaccinated mice, CD4+ T cells were the dominant cell subset recorded from L-p-omp25 [X1] vaccinated mice. From these data it is not possible to determine whether this difference in phenotype of primed effector cells had any significant impact upon the development and maintenance of protective immunity, as both of these single dose preparations induced equivalent weak protective effects despite the involvement of distinct T cell subsets.

The CD4+ and CD8+ effector cells generated by naked p-omp25 vaccination are likely to be the result of myocyte transfection and antigen production, followed by antigen uptake by a professional APC and processing via conventional MHC class II pathways and cross presentation to access MHC class I pathways. Intramuscular delivery of naked DNA is not considered an efficient way to delivery DNA directly to APCs, and other studies have suggested that cross-presentation is the dominant route of CD8+ priming in this situation. The relative abundance of the CD8+ T cell subset demonstrated in this study suggests that the naked DNA derived Omp25 antigen readily accesses the MHC class I processing pathways, either because of effective direct transfection of professional APCs, or because of intrinsic properties of the protein which target it to the cytosol of APCs.

DNA vaccines were surface adsorbed onto cationic liposomes to promote efficient uptake of DNA into cells. Direct uptake of liposomes by professional APCs may also enhance immune induction in the draining lymph nodes, and increased potential for MHC class I restricted presentation of endogenously produced DNA encoded antigens and direct priming of CD8+ T cells. However, the L-p-omp25 [X1] vaccine was not able to produce the total numbers of effector cells achieved by either the protective p-omp25 [X4] vaccination or the less effective p-omp25 [X1] vaccination. Depletion studies indicated that CD4+ T cells are the dominant responders to the L-p-omp25 [X1] vaccine. Moreover, the actual frequency of antigen specific CD4+ T cells elicited by p-omp25 [X1], p-omp25 [X4], or L-p-omp25 [X1] was not significantly different ($p>0.05$), suggesting that the principal difference between the vaccines was that liposome formulation was less effective than naked DNA for presenting antigen in association with MHC class I for priming CD8+ T cells.

Post-challenge ELISPOT investigations revealed that all mice contained Omp25 specific effector cells post-exposure to live *Brucella*. In most cases the frequency of cells was above the analytical capacity of the assay, and resulted in saturated readings (>500 SFC/$10^6$), suggesting that native Omp25 is a prominent and significant immunogen in live *B. melitensis* 16M infections. A significant difference in IFN-γ generation between groups that had been primed by vaccination compared to that from pre-challenge antigen naïve mice was not observed. An investigation of effector cells at an earlier interval post-challenge may have revealed an anamnestic response from the Omp25 responsive mice. However, at 15 days post-challenge it appears that the strong primary Omp25 specific response observed in naïve mice may mask this effect.

Although an explanation for specific abrogation of CD8+ priming by liposome vaccination is not apparent, these data clearly indicate that the CD8+ effector cells are important contributors to the protective effect of the omp25 based vaccines. A clear relationship between the number of CD8+ effector cells (Total SFC-CD8+ depleted SFC) and protective effect is evident. In contrast, a clear correlation between CD4+ effector cells and protection is not observed. Overall, these results suggest that CD8+ T cells are the main effectors of the protective response of p-omp25 vaccination. Furthermore, these data indicate that the liposome delivery strategy is not useful as a mechanism through which to achieve increased uptake and immunogenicity, and protective efficacy of the p-omp25 vaccine.

p-ialB Specific Immunity

Single Versus Multiple Dose Naked DNA Vaccination

Studies with the p-ialB vaccine showed that multiple inoculations of the naked DNA vaccine (p-ialB [X4]) was a more immunogenic and efficacious strategy compared with single inoculations of the naked DNA vaccine (p-ialB [X1]) and liposome-adsorbed vaccine (L-p-ialB [X1]). In this respect these data concur with that from the p-omp25 studies. However there were several differences in the data from the p-ialB studies compared to the p-omp25 studies suggesting a different mode of action for these two protective vaccines.

Antibody production was the most striking output of the immune response following p-ialB [X4] vaccination: high titer equally balanced IgG1 and IgG2a responses were detected. A single dose of naked DNA (p-ialB [X1]) was unable to induce detectable levels of antibody. Similarly, significant IFN-γ secreting cells were only observed from the p-ialB [X4] protective vaccination regime. IFN-γ secretion was mainly attributed to CD4+ cells, with the bias toward MHC class II primed immune responses resulting from secretion of the endogenously manufactured protein and hence supplying antigen for exogenous uptake. Antigen secretion also increases the availability of the IalB protein for interaction with B cells, thus promoting strong antibody responses. In general, it was shown that that the protective effect of p-ialB [X4] vaccination correlated to the induction of high titer specific antibody and a CD4+ dominated cellular response.

Unlike the single dose p-omp25 [X1] DNA vaccine the p-ialB [X1] vaccine did not induce measurable antigen specific IFN-γ production. Since the quantity of DNA delivered in these experiments was, as near as practicable, equivalent, the discrepancy in immunogenicity suggests that the IalB antigen may be inherently less immunogenic than the Omp25 antigen. Indirect evidence suggesting that IalB is a comparatively weak immunogen can be found through measurement of the IalB specific response of Rev.1 and 16M infected mice. It is notable that IalB specific effector cells or antibodies are not detected from mice that have been vaccinated with Rev.1 or from IalB naïve mice that have been challenged with *B. melitensis* 16M. This suggests that the native antigen is either poorly expressed or poorly immunogenic, and indicates that IalB specific immune responses are not essential for the development of Rev.1 mediated protection.

Differences in plasmid structure between p-omp25 and p-ialB may account for slight differences in immunogenicity. Enhanced expression from pTargeT-omp25 may account for the more rapid induction of Omp25 specific responses that are detected after a single inoculation. This modest improvement in immunogenicity is only observed as a more rapid induction of specific response and does not the impact on the overall magnitude of the specific response. When pTargeT-omp25 (with intron element) and pCR3.1-omp25 (without intron element) were directly compared (data not shown) differences in the magnitude or rapidity of the Omp25 specific response of mice treated with the different vaccines was not observed.

Nevertheless, this apparent poor immunogenicity is overcome by multiple inoculations of p-ialB since IalB specific CD4+ and antibodies generated by p-ialB [X4] vaccination are highly effective for the control of *B. melitensis* in the murine host.

Liposome Versus Naked DNA Vaccination

IalB specific antibody was detected following a single dose of L-p-ialB compared to three doses of naked p-ialB, indicating that liposome formulation of the p-ialB vaccine prompted more rapid induction of immune responses compared to naked DNA vaccination. This effect may be due to a more effective uptake of L-p-ialB by APCs, resulting in a faster delivery of antigen to the LNs and other sites of immune induction. Antigen specific effector cells were not apparent in the L-p-ialB vaccinated mice prior to challenge. It was surprising therefore that the post-challenge ELISPOT data from the p-ialB investigations indicated that only p-ialB [X4] and L-p-ialB vaccinated mice had measurable IalB specific IFN-γ production post-exposure to virulent *B. melitensis* 16M, suggesting an anamnestic response from these animals. In the post-challenge studies the number of antigen specific effector cells observed from L-p-ialB inoculated mice was considerably increased to that observed in p-ialB [X1] inoculated mice thereby providing further evidence of enhanced immunogenicity of the liposome formulation.

EXAMPLE 3

Vaccination with p-ialB and Differential Diagnosis

A naked DNA vaccine encoding the putative invasion protein B (ialB) has been shown to have significant protective effect against virulent challenge in a mouse model of brucellosis (Commander et al., 2003, supra; see also Example 1). Inoculation elicits production of IalB-specific antibodies and Th1 cellular immune responses that not only provides protection against challenge but, as shown below, can also be used to confirm exposure to the vaccine. Moreover we have found that since the response is restricted to the IalB antigen of the *Brucella* organism, true infection can be distinguished from vaccination.

Diagnosis of *Brucella* infection can be achieved via Complement Fixation Test, Serum Agglutination Test, Rose Bengal antigen Test, and ELISA methods. Routine surveillance for brucellosis is carried out in the UK and often in other countries using a simple indirect ELISA ("iELISA") method. The antigen used in the ELISA is a crude preparation of *Brucella* LPS. The LPS of *Brucella* is the serodominant antigen associated with smooth strain infections of *Brucella*. Vaccines such as *B. abortus* S. 19 and *B. melitensis* Rev.1 are live attenuated smooth strain infections and therefore induce LPS specific immune responses that cannot readily be distinguished from that associated with a virulent infection. Thus vaccination with these organisms is inappropriate (and in many cases illegal) during control and eradication campaigns based upon test and slaughter. Therefore one of the potential advantages of vaccine p-ialB is that it does not evoke anti-LPS responses, and hence vaccinated or protected animals can be distinguished from infected 'reactors'. To test this hypothesis, mice receiving p-ialB vaccination were tested in a modified version of the standard *Brucella* iELISA diagnostic test.

Materials and Methods

Sera was collected from vaccinated mice at intervals post-vaccination, and tested using (a) an IaIB specific indirect ELISA, (b) a crude 16M antigen, and (c) a modified version of the standard *Brucella* iELISA used in routine diagnosis. These methods are described above. The iELISA was modified to test mouse sera at dilutions of 1/10, 1/100 and 1/1000 through the use of anti-mouse IgG Horse Radish Peroxidase conjugate at 1/4000. All other reagents and conditions were unchanged from the standard protocol. SAT and CFT tests were also modified for test of mouse sera.

Results

The detection of a recombinant IaIB or 16M specific antibody response has been previously described (see above).

Each of the samples tested in this assay was also tested in the modified LTD/*Brucella* iELISA. A modest response was detected from Rev.1 vaccinated mice in this test. All other test samples were negative in this ELISA. All mouse sera were negative in the CFT and RBT assays (including the Rev.1 mouse sera).

Discussion

The results from this investigation suggest that the iELISA antigen does not react with sera from p-iaIB vaccinated mice. Since the IaIB protein of *Brucella* is believed to be a soluble secreted antigen, it is believed that the crude iELISA (a phenol extracted LPS) is devoid of the IaIB antigen and this absence permits discrimination of the p-iaIB vaccinated mice from the mice vaccinated with the Rev.1 strain or infected with the 16M strain of *Brucella*. Extension of this finding to sheep and goats (and other potential target species) makes the p-iaIB vaccine applicable for use during a test and slaughter based eradication campaign without the need for development of novel diagnostic tests.

An infected animal would test positive in the standard iELISA and also would be likely to test positive in an IaIB specific ELISA. A p-iaIB vaccinated animal, would not present a positive result in the traditional iELISA, but exposure to the vaccination could be monitored using an IaIB specific ELISA.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents cited herein are incorporated by reference in their entirety, regardless of whether this has been specifically stated for each document.

What is claimed is:

1. An immunogenic nucleic acid composition comprising DNA encoding the polypeptide *Brucella melitensis* Invasion Protein B having an amino acid sequence as shown in SEQ ID NO: 12; and an adjuvant, wherein said adjuvant is a liposome.

2. A DNA vaccine composition comprising a plasmid vector having DNA encoding the polypeptide *Brucella melitensis* Invasion Protein B having an amino acid sequence as shown in SEQ ID NO: 12; in which said plasmid vector is adsorbed to a liposome.

3. The composition of claim 1 or 2, which when administered to an animal subject induces an immune response that is characterized by enhancement of T cell priming and/or antibody generation compared with an immune response induced by a naked DNA vaccine encoding the corresponding polypeptide.

4. The composition of claim 1 or 2, wherein said liposome is a cationic liposome.

5. The composition of claim 1 or 2, wherein said DNA is passively adsorbed to said liposome.

6. The composition of claim 1 or 2, wherein said DNA comprises the nucleotide sequence of SEQ ID NO: 11.

7. A lipid-formulated vaccine comprising DNA encoding the polypeptide *Brucella melitensis* Invasion Protein B having an amino acid sequence as shown in SEQ ID NO: 12.

8. The vaccine of claim 7, wherein said DNA comprises the nucleotide sequence of SEQ ID NO: 11.

9. A method of inducing an enhanced immune response to *Brucella* infection in an animal, comprising administering to said animal an effective amount of the composition of claim 1 or 2, or the vaccine of claim 7, thereby inducing an enhanced immune response which is characterized in that it is greater in magnitude than an immune response induced by a naked DNA vaccine encoding the corresponding polypeptide.

10. The method of claim 9, wherein said enhanced immune response is characterized by increased antibodies.

11. The method of claim 9 or 10, wherein said enhanced immune response is characterized by enhanced T cell priming.

12. The method of claim 9, in which said animal is a mammal.

* * * * *

SEQUENCE LISTING

```
<160> NUMBER OF SEQ ID NOS: 12

<210> SEQ ID NO 1
<211> LENGTH: 35
<212> TYPE: DNA
<213> ORGANISM: Artificial
<220> FEATURE:
<223> OTHER INFORMATION: PRIMER

<400> SEQUENCE: 1

aaactcgagc cgccaccatg cgcactctta agtct                              35


<210> SEQ ID NO 2
<211> LENGTH: 29
<212> TYPE: DNA
<213> ORGANISM: Artificial
<220> FEATURE:
<223> OTHER INFORMATION: PRIMER

<400> SEQUENCE: 2

aaatctagaa ccggatgcct gaaatcctt                                     29


<210> SEQ ID NO 3
<211> LENGTH: 31
<212> TYPE: DNA
<213> ORGANISM: Artificial
<220> FEATURE:
<223> OTHER INFORMATION: PRIMER

<400> SEQUENCE: 3

aaaggatccg ccaccatgaa aaattatcgt g                                  31


<210> SEQ ID NO 4
<211> LENGTH: 30
<212> TYPE: DNA
<213> ORGANISM: Artificial
<220> FEATURE:
<223> OTHER INFORMATION: PRIMER
```

-continued

<400> SEQUENCE: 4
aaagaattct tacttggtca atgcctgaat 30

<210> SEQ ID NO 5
<211> LENGTH: 21
<212> TYPE: DNA
<213> ORGANISM: Artificial
<220> FEATURE:
<223> OTHER INFORMATION: PRIMER

<400> SEQUENCE: 5
tgcgcaactc ttaagtctct t 21

<210> SEQ ID NO 6
<211> LENGTH: 21
<212> TYPE: DNA
<213> ORGANISM: Artificial
<220> FEATURE:
<223> OTHER INFORMATION: PRIMER

<400> SEQUENCE: 6
ttagaacttg tagccgatgc c 21

<210> SEQ ID NO 7
<211> LENGTH: 20
<212> TYPE: DNA
<213> ORGANISM: Artificial
<220> FEATURE:
<223> OTHER INFORMATION: PRIMER

<400> SEQUENCE: 7
atggcgaaag aagaagtcct 20

<210> SEQ ID NO 8
<211> LENGTH: 20
<212> TYPE: DNA
<213> ORGANISM: Artificial
<220> FEATURE:
<223> OTHER INFORMATION: PRIMER

<400> SEQUENCE: 8
actagaacct tgtcaccggc 20

<210> SEQ ID NO 9
<211> LENGTH: 723
<212> TYPE: DNA
<213> ORGANISM: Brucella melitensis

<400> SEQUENCE: 9
atgcgcactc ttaagtctct cgtaatcgtc tcggctgcgt tgctgccgtt ctctgcgacc 60
gcttttgctg ccgacgccat ccaggaacag cctccggttc cggctccggt tgaagtagct 120
ccccagtata gctgggctgg tggctatacc ggtctttacc ttggctacgg ctggaacaag 180
gccaagacca gcaccgttgg cagcatcaag cctgacgatt ggaaggctgg cgcctttgct 240
ggctggaact tccagcagga ccagatcgta tacggtgttg aaggtgatgc aggttattcc 300
tgggccaaga agtccaagga cggcctggaa gtcaagcagg gctttgaagg ctcgctgcgt 360
gcccgcgttg gctacgacct gaacccggtt atgccgtacc tcacggctgg tattgccggt 420
tcgcagatca agcttaacaa cggcttggac gacgaaagca agttccgcgt gggttggacg 480
gctggtgccg gtctcgaagc caagctgacg gacaacatcc tcggccgcgt tgagtaccgt 540
tacacccagt acggcaacaa gaactatgat ctggccggta cgactgttcg caacaagctg 600

-continued

```
gacacgcagg atttccgcgt cggcatcggc tacaagttct aattatagca taattggaca    660

cggaaaaccg gacaggcaac tgtccggttt tttgttgtct gcaaaggatt tcaggcatcc    720

ggt                                                                  723


<210> SEQ ID NO 10
<211> LENGTH: 213
<212> TYPE: PRT
<213> ORGANISM: Brucella melitensis

<400> SEQUENCE: 10

Met Arg Thr Leu Lys Ser Leu Val Ile Val Ser Ala Ala Leu Leu Pro
1               5                   10                  15

Phe Ser Ala Thr Ala Phe Ala Ala Asp Ala Ile Gln Glu Gln Pro Pro
            20                  25                  30

Val Pro Ala Pro Val Glu Val Ala Pro Gln Tyr Ser Trp Ala Gly Gly
        35                  40                  45

Tyr Thr Gly Leu Tyr Leu Gly Tyr Gly Trp Asn Lys Ala Lys Thr Ser
    50                  55                  60

Thr Val Gly Ser Ile Lys Pro Asp Asp Trp Lys Ala Gly Ala Phe Ala
65                  70                  75                  80

Gly Trp Asn Phe Gln Gln Asp Gln Ile Val Tyr Gly Val Glu Gly Asp
                85                  90                  95

Ala Gly Tyr Ser Trp Ala Lys Lys Ser Lys Asp Gly Leu Glu Val Lys
            100                 105                 110

Gln Gly Phe Glu Gly Ser Leu Arg Ala Arg Val Gly Tyr Asp Leu Asn
        115                 120                 125

Pro Val Met Pro Tyr Leu Thr Ala Gly Ile Ala Gly Ser Gln Ile Lys
    130                 135                 140

Leu Asn Asn Gly Leu Asp Asp Glu Ser Lys Phe Arg Val Gly Trp Thr
145                 150                 155                 160

Ala Gly Ala Gly Leu Glu Ala Lys Leu Thr Asp Asn Ile Leu Gly Arg
                165                 170                 175

Val Glu Tyr Arg Tyr Thr Gln Tyr Gly Asn Lys Asn Tyr Asp Leu Ala
            180                 185                 190

Gly Thr Thr Val Arg Asn Lys Leu Asp Thr Gln Asp Phe Arg Val Gly
        195                 200                 205

Ile Gly Tyr Lys Phe
    210


<210> SEQ ID NO 11
<211> LENGTH: 522
<212> TYPE: DNA
<213> ORGANISM: Brucella melitensis

<400> SEQUENCE: 11

atgaaaaatt atcgtgcaat cggtcttgca ttcacgttca ctgccctttc cagtctttcg     60

gcctttgcag cctccctgcc cggcggagca agcaccttgc aggaaaccta tcaggactgg    120

accgtgtctt gccagtcgca gaaggataca acagcctgcg tgatgcgtca ggagcaaagc    180

agcgcccagg ccggccagcg cgttctgact gccgagctgc gcaacgtcgc cggcggcaaa    240

gttgacggtg tgttgctgat gccgttcggt cttgatcttg ccaagggcgc ctcgctcaag    300

attgatgaca ccgctgggcc aaacctcacc ttctccacct gcctgccgca gggctgcctc    360

gcgccagtga gcttcgatgc caagcaggtt gctgcgctga aatccggcac caacatcaat    420
```

-continued

```
gtcaccacga cggcgctcag cccgagccag ccggttgcct tcaagatttc cctgaaaggc    480

ttcggtgccg cgctcgaccg cattcaggca ttgaccaagt aa                       522


<210> SEQ ID NO 12
<211> LENGTH: 173
<212> TYPE: PRT
<213> ORGANISM: Brucella melitensis

<400> SEQUENCE: 12

Met Lys Asn Tyr Arg Ala Ile Gly Leu Ala Phe Thr Phe Thr Ala Leu
1               5                   10                  15

Ser Ser Leu Ser Ala Phe Ala Ala Ser Leu Pro Gly Gly Ala Ser Thr
            20                  25                  30

Leu Gln Glu Thr Tyr Gln Asp Trp Thr Val Ser Cys Gln Ser Gln Lys
        35                  40                  45

Asp Thr Thr Ala Cys Val Met Arg Gln Glu Gln Ser Ser Ala Gln Ala
    50                  55                  60

Gly Gln Arg Val Leu Thr Ala Glu Leu Arg Asn Val Ala Gly Gly Lys
65                  70                  75                  80

Val Asp Gly Val Leu Leu Met Pro Phe Gly Leu Asp Leu Ala Lys Gly
                85                  90                  95

Ala Ser Leu Lys Ile Asp Asp Thr Ala Gly Pro Asn Leu Thr Phe Ser
            100                 105                 110

Thr Cys Leu Pro Gln Gly Cys Leu Ala Pro Val Ser Phe Asp Ala Lys
        115                 120                 125

Gln Val Ala Ala Leu Lys Ser Gly Thr Asn Ile Asn Val Thr Thr Thr
    130                 135                 140

Ala Leu Ser Pro Ser Gln Pro Val Ala Phe Lys Ile Ser Leu Lys Gly
145                 150                 155                 160

Phe Gly Ala Ala Leu Asp Arg Ile Gln Ala Leu Thr Lys
                165                 170
```